(12) United States Patent
Urabe et al.

(10) Patent No.: US 9,220,477 B2
(45) Date of Patent: Dec. 29, 2015

(54) ULTRASONIC DIAGNOSTIC DEVICE, AND REGION-TO-BE-DETECTED IMAGE DISPLAY METHOD AND MEASUREMENT METHOD USING SAME

(75) Inventors: Makiko Urabe, Tokyo (JP); Koetsu Saito, Tokyo (JP); Akihiro Kawabata, Kanagawa (JP); Manabu Migita, Kanagawa (JP); Morio Nishigaki, Kanagawa (JP); Ryuichi Kato, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 13/515,904

(22) PCT Filed: Dec. 17, 2010

(86) PCT No.: PCT/JP2010/007340
§ 371 (c)(1),
(2), (4) Date: Jun. 14, 2012

(87) PCT Pub. No.: WO2011/074271
PCT Pub. Date: Jun. 23, 2011

(65) Prior Publication Data
US 2012/0296214 A1  Nov. 22, 2012

(30) Foreign Application Priority Data

Dec. 18, 2009  (JP) ................. 2009-287126

(51) Int. Cl.
*A61B 8/14* (2006.01)
*A61B 8/00* (2006.01)
(Continued)

(52) U.S. Cl.
CPC ............. *A61B 8/4444* (2013.01); *A61B 8/0858* (2013.01); *A61B 8/0891* (2013.01);
(Continued)

(58) Field of Classification Search
None
See application file for complete search history.

(56) References Cited

U.S. PATENT DOCUMENTS 5,782,768 A * 7/1998 Hashimoto et al. ........... 600/443
7,500,952 B1 * 3/2009 Chiang et al. ................. 600/446
(Continued)

FOREIGN PATENT DOCUMENTS

JP      04152940 A  *  5/1992
JP      4189405 B       9/2008
(Continued)

OTHER PUBLICATIONS

International Search Report for corresponding International Application No. PCT/JP2010/007340 mailed Mar. 8, 2011.
(Continued)

*Primary Examiner* — Long V Le
*Assistant Examiner* — Kevin Pontius
(74) *Attorney, Agent, or Firm* — Lucas & Mercanti, LLP

(57) ABSTRACT

An ultrasonic diagnostic apparatus includes a controller, to which a probe and a monitor are connected, the probe having an array of transducers, in which a number of transducers are arranged in a first direction. The controller controls transmission of an ultrasonic beam using the array of transducers and reception of an echo signal reflected from a region of interest, generates image data based on the echo signal, and gets echo signals received from multiple points of the region of interest by either moving or swinging the array of transducers in a second direction that intersects with the first direction at right angles. If the sum of image data ranges of measured value retrievable portions of the region of interest at the multiple points synthesized based on the echo signals, is equal to or greater than a predetermined value, the controller calculates a detected value of the region of interest.

18 Claims, 26 Drawing Sheets

(51) Int. Cl.
  *A61B 8/08* (2006.01)
  *G01S 7/52* (2006.01)
  *G01S 15/89* (2006.01)

(52) U.S. Cl.
  CPC .............. *A61B 8/463* (2013.01); *G01S 7/5205* (2013.01); *G01S 7/52073* (2013.01); *G01S 7/52074* (2013.01); *G01S 15/894* (2013.01); *G01S 15/8915* (2013.01); *A61B 8/4461* (2013.01); *A61B 8/4483* (2013.01); *A61B 8/461* (2013.01)

(56) References Cited

U.S. PATENT DOCUMENTS

| | | | | |
|---|---|---|---|---|
| 7,959,572 | B2* | 6/2011 | Ishihara | 600/437 |
| 8,079,958 | B2* | 12/2011 | Satoh et al. | 600/443 |
| 8,133,181 | B2* | 3/2012 | Yuk et al. | 600/443 |
| 8,172,754 | B2* | 5/2012 | Watanabe et al. | 600/443 |
| 8,439,839 | B2* | 5/2013 | Kadokura et al. | 600/438 |
| 2005/0131295 | A1* | 6/2005 | Li | 600/443 |
| 2007/0055149 | A1 | 3/2007 | Suzuki et al. | |
| 2009/0030326 | A1 | 1/2009 | Kim et al. | |
| 2009/0204007 | A1 | 8/2009 | Katoh et al. | |
| 2010/0185090 | A1* | 7/2010 | Suzuki et al. | 600/443 |
| 2010/0210946 | A1* | 8/2010 | Harada et al. | 600/443 |
| 2012/0296213 | A1* | 11/2012 | Mauldin et al. | 600/443 |

FOREIGN PATENT DOCUMENTS

| | | | |
|---|---|---|---|
| JP | 2008-272338 | A | 11/2008 |
| JP | 2009-089911 | A | 4/2009 |
| JP | 2009-291269 | A | 12/2009 |
| WO | WO2008068932 | A1 * | 6/2008 |
| WO | 2009/013871 | A1 | 1/2009 |
| WO | WO2009047966 | A1 * | 4/2009 |

OTHER PUBLICATIONS

Stein et al., "Use of Carotid Ultrasound to Identify Subclinical Vascular Disease and Evaluate Cardiovascular Disease Risk: A Consensus Statement from the American Society of Echocardiography Carotid Intima-Media Thickness Task Force", Journal of the American Society of Echocardiography, Feb. 2008, pp. 93-111.

Extended European Search Report corresponding to PCT application No. PCT/JP2010/007340 dated Jun. 20, 2013.

Chinese Office Action, Application No. 201080047038.4, mailing date: Jan. 14, 2014 (10 pages).

English language translation of Chinese Office Action, Application No. 201080047038.4, mailing date: Jan. 14, 2014 (19 pages).

EP Office Action, Application No. 10 837 302.8-1660, Dated: Feb. 20, 2014 (4 pages).

* cited by examiner

FIG.17
(a)
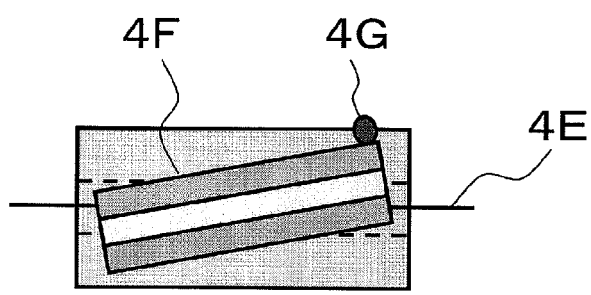
(b)
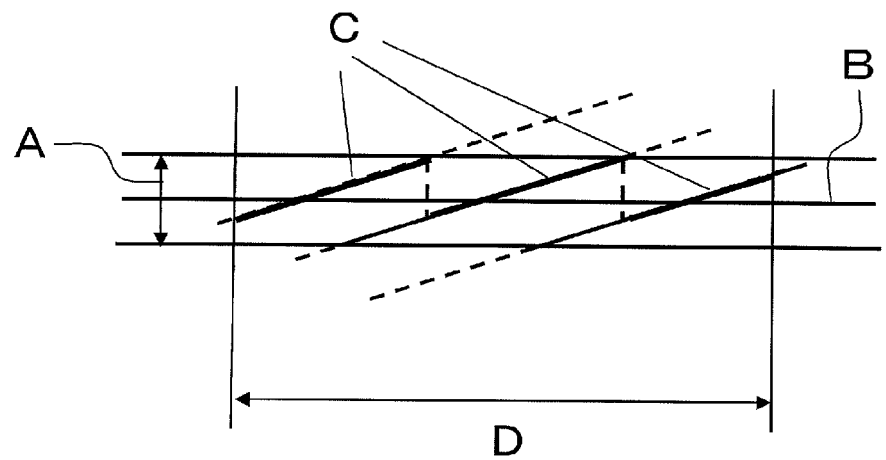

ULTRASONIC DIAGNOSTIC DEVICE, AND REGION-TO-BE-DETECTED IMAGE DISPLAY METHOD AND MEASUREMENT METHOD USING SAME

TECHNICAL FIELD

The present invention relates to an ultrasonic diagnostic apparatus and a method of carrying out a measurement using the apparatus.

BACKGROUND ART

In recent years, an ultrasonic diagnostic apparatus has captured a spotlight as an apparatus for detecting the status of a carotid artery, for example. An ultrasonic diagnostic apparatus generally has the following structure.

Specifically, an ultrasonic diagnostic apparatus includes a probe, a controller that is connected to the probe, and a monitor that is connected to the controller. The ultrasonic diagnostic apparatus generates an image representing a region of interest (ROI) such as the carotid artery based on an ultrasonic beam that has been received from the probe, and displays that image on the monitor (see Non-Patent Document No. 1, for example).

Non-Patent Document No. 1 mentions the measurement of an intima-media thickness (which will be abbreviated herein as "IMT") as a method for detecting the status of a carotid artery. The "IMT" means the thickness of an intima-media complex in the vascular wall of a carotid artery. In general, when the IMT is measured, an IMT measuring range is set along the carotid artery and the maximum thickness (max IMT) or mean thickness (mean INT) is measured within that range. For example, Non-Patent Document No. 1 recommends that such an IMT measuring range have a length of 1 cm.

CITATION LIST

Non-Patent Literature

Non-Patent Document No. 1: Journal of the American Society of Echocardiography, February 2008 (pp. 93 to 111)

SUMMARY OF INVENTION

Technical Problem

As disclosed in Non-Patent Document No. 1, if the status of a carotid artery, which is the region of interest (ROI), is going to be checked (e.g., if its IMT is going to be measured), however, nobody but a well experienced skilled person could make an accurate measurement, which is a problem with the prior art.

The reason is that to check the status of a carotid artery using a conventional apparatus, the probe should be put exactly at a position where the center axis of the carotid artery can be cut vertically or perpendicularly and an ultrasonic beam should be sent from there. However, neither the position nor shape of the carotid artery can be seen from over the surface of the subject's neck. In addition, the position and shape of the carotid artery will vary quite a little from one person to another. That is why nobody but a well-trained skilled person could put a probe at such a position where the center axis of the carotid artery can be cut vertically and could get the measurement done accurately.

It is therefore an object of the present invention to provide an ultrasonic diagnostic apparatus that enables not just such a skilled person but also anybody else to get the measurement done accurately and also provide a method of carrying out a measurement on a region of interest using such an apparatus.

Solution to Problem

An ultrasonic diagnostic apparatus according to the present invention includes a controller, to which a probe and a monitor are connected, the probe having an array of transducers, in which a number of transducers are arranged in a first direction. The controller controls transmission of an ultrasonic beam using the array of transducers of the probe and reception of an echo signal, which is a wave of the ultrasonic beam that has been reflected from a region of interest, generates image data based on the echo signal, gets echo signals received from multiple points of the region of interest by either moving or swinging the array of transducers in a second direction that intersects with the first direction at right angles, and if the sum of image data ranges of measured value retrievable portions of the region of interest, which are included in tomographic images at the multiple points that have been synthesized based on the echo signals, is equal to or greater than a predetermined value, calculates a detected value of the region of interest.

The ultrasonic diagnostic apparatus may further include the probe to be connected to the controller. The controller may have a detection mode in which a status of the region of interest is detected, and in which the probe receives echo signals that are associated with multiple cross sections of the region of interest and if the sum of the image data ranges of the measured value retrievable portions of the region of interest, which are included in the multiple cross sections, is equal to or greater than a predetermined value, the controller may calculate the detected value of the region of interest.

The ultrasonic diagnostic apparatus may further include the monitor which displays an image based on the image data that has been generated by the controller.

The controller may have a positioning mode to be carried out before the detection mode. In the positioning mode, the controller may generate not only image data representing the region of interest based on the echo signal but also image data representing the tilted positioning which indicates how much the probe is tilted with respect to the region of interest. Based on the image data detected, the monitor may display the image representing the region of interest and the image representing the tilted positioning.

The image representing the improperly tilted positioning may include a centerline representing the center axis of the region of interest to be detected by the probe and a probe symbol indicating how much the probe is tilted with respect to the centerline.

A probe origin marker may have been set on the probe, and the probe symbol may include a probe origin that corresponds to the probe origin marker and that indicates a position on the image representing the tilted positioning.

On the image representing the tilted positioning, detectable lines, indicating that the region of interest is detectable, may be rendered on both sides of the centerline of the region of interest.

The probe may have three arrays of transducers, which are arranged in three parallel lines in the first direction.

The probe may include a swinging section that swings the array of transducers under the control of the controller.

The probe may include ultrasonic transducers, which are arranged in three or more lines at least in the first direction so as to form a matrix pattern as a whole.

In an alternative ultrasonic diagnostic apparatus, the swinging section may swing the array of transducers on the axis of swing in accordance with an instruction given by the controller so that the array defines a predetermined swing angle with respect to the center of swing of the array of transducers. And the controller may control swinging so that the swing angle of the probe becomes greater in the positioning mode than in the detection mode.

The probe origin marker of the probe may be set at an end of the array of transducers.

The controller may have a positioning mode to be carried out before the detection mode. In the positioning mode, the controller may generate not only image data for positioning based on an echo signal that has been obtained by sending an ultrasonic beam in the second direction with some of the transducers in the array controlled but also first image data for detection of the region of interest based on an echo signal that has been obtained by sending an ultrasonic beam in the second direction with the other transducers in the array controlled. On the other hand, in the detection mode, the controller may generate second image data for detection of the region of interest by controlling all transducers in the array, and the monitor may display the image for detection based on the second image data for detection.

Those transducers that are used in the array to generate the positioning image may scan the body with an ultrasonic beam either mechanically or by deforming a material, which is arranged on the array of transducers so as to face the body and be deformed with an applied voltage.

The material deformed with the applied voltage may be a conductive high molecular material, an ionic conductive high molecular material or a dielectric elastomer.

The monitor may further render a guideline for positioning on the image for positioning.

The array of transducers of the probe may include multiple subsets of transducers, each said subset being used to generate the image for positioning. The controller may generate image data for positioning that is associated with either each said subset of transducers or only selected subsets of transducers. And the monitor may display the image for positioning based on each said image data for positioning.

An ROI measuring method according to the present invention is a method of carrying out a measurement on a region of interest using the ultrasonic diagnostic apparatus of the present invention. The method includes the steps of: putting the probe of that ultrasonic diagnostic apparatus on a body; making the probe receive echo signals from multiple points in the region of interest; checking a status of the region of interest in respective tomographic images that are associated with the multiple points and that have been synthesized based on the echo signal; and if the sum of image data ranges of measured value retrievable portions of the region of interest has turned out to be equal to or greater than a predetermined value in the step of checking the status of the region of interest, then calculating the detected value of the region of interest.

An ROI image monitoring method according to the present invention is a method of displaying an image representing a region of interest using an ultrasonic diagnostic apparatus. The method includes the steps of: putting the probe of the alternative ultrasonic diagnostic apparatus of the present invention on a body; displaying, on the monitor, an image representing how much the probe is tilted with respect to the region of interest of the body based on image data representing the tilted positioning; adjusting the position of the probe based on an image representing the tilted positioning to be displayed on the monitor either while the probe is being moved or after the probe has been moved; and displaying the image of the region of interest on the monitor based on the image data of the region of interest.

The step of putting may include putting the probe on a neck of the body, and the step of displaying the image of the region of interest may include displaying an image representing a carotid artery.

Advantageous Effects of Invention

One preferred embodiment of the present invention includes a controller, to which a probe and a monitor are connected. The controller has a detection mode in which multiple detected images, detected from multiple points and generated by moving the probe with respect to the region of interest, are displayed on the monitor. In addition, if the sum of (appropriate) image data ranges of measured value retrievable portions of the region of interest, which are included in those images detected from the multiple points, is equal to or greater than a predetermined value, a detected value is calculated with respect to the region of interest. As a result, accurate detection can also get done even by an unskilled person.

A controller is provided, to which a probe and a monitor are connected, the probe having an array of transducers, in which a number of transducers are arranged. The controller has a positioning mode and a detection mode. In the positioning mode, the object is scanned with an ultrasonic beam substantially perpendicularly to the array of transducers using some of the transducers in the array, thereby obtaining a positioning image to get positioning done. And when the modes of operation are changed into the detection mode after that, the positioning image is switched into the detected image using the array of transducers including those transducers that have been used to generate the positioning image. Consequently, even an unskilled person can also make an accurate detection.

That is to say, according to the present invention, only if the sum of (appropriate) image data ranges of measured value retrievable portions, which are included in multiple images detected from the multiple points, is equal to or greater than a predetermined value, the detected value of the region of interest is supposed to be calculated. That is why even if the relative position of the probe with respect to the region of interest is slightly different from the proper one, the detected value can still be obtained from the region of interest. Consequently, even an unskilled person can also make an accurate detection.

BRIEF DESCRIPTION OF DRAWINGS

FIG. 17(a) illustrates a state in which a portion of the probe with a probe origin is slightly improperly tilted outward with respect to the centerline representing the center axis of the carotid artery and FIG. 17(b) illustrates a specific detection position C that falls within not only a predetermined length defined by the image data representing the measured value retrievable region (i.e., appropriate image data) to detect the IMT but also the detectible range (width).

DESCRIPTION OF EMBODIMENTS

Hereinafter, preferred embodiments of an ultrasonic diagnostic apparatus according to the present invention will be described with reference to the accompanying drawings.

Embodiment 1

Figure 1:
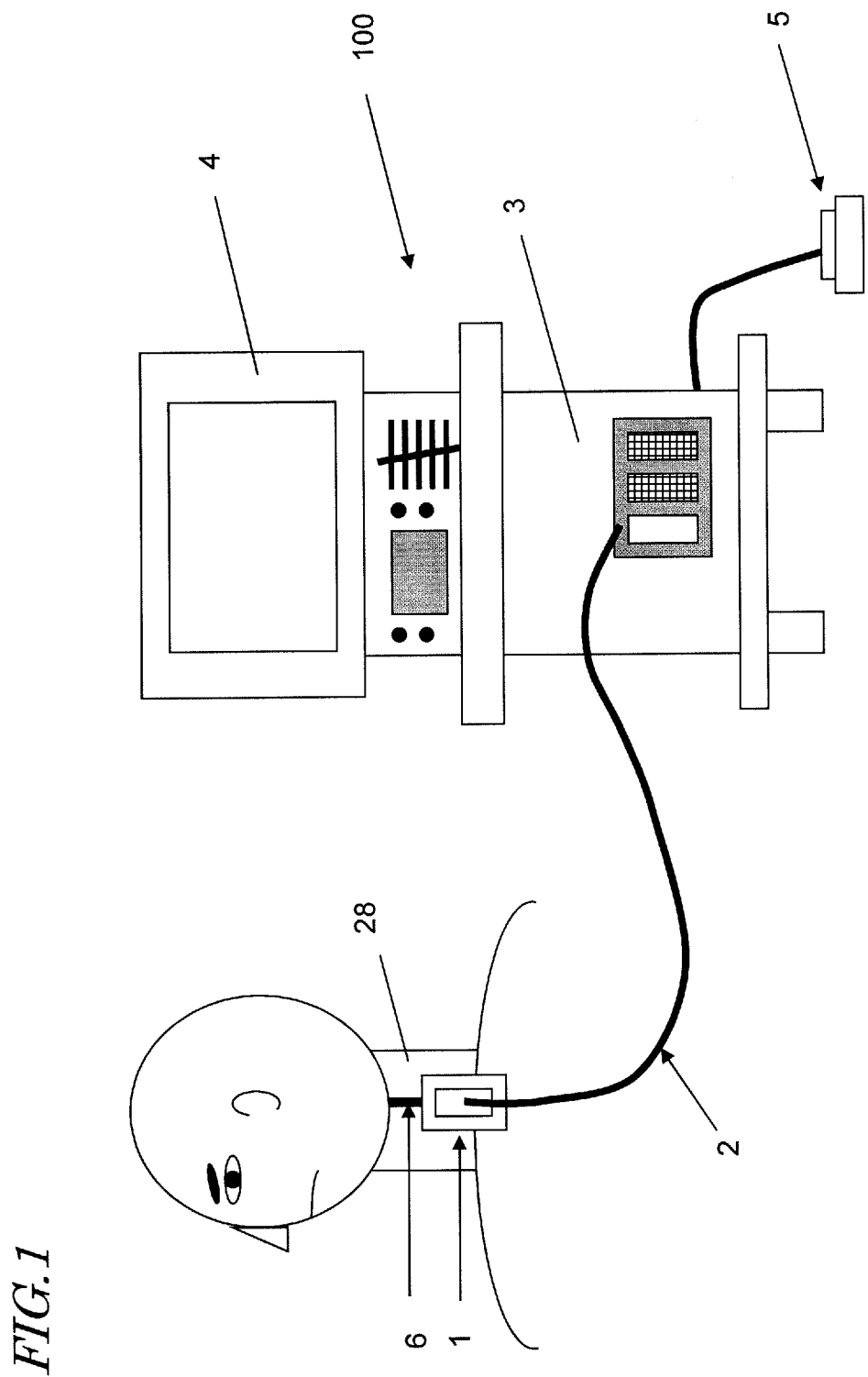
FIG. 1 illustrates the appearance of an ultrasonic diagnostic apparatus 100 according to the present invention.

FIG. 1 illustrates the appearance of an ultrasonic diagnostic apparatus 100 as a first specific preferred embodiment of the present invention. The ultrasonic diagnostic apparatus 100 includes a probe 1, a controller 3, to which the probe 1 is connected with a cable 2, a monitor 4, which is also connected to the controller 3, and a foot switch 5.

The probe 1 sends an ultrasonic beam that has been output from the controller 3 toward a target tissue inside an organism and receives an echo signal that has been reflected back from the tissue in the organism. Then, the probe 1 outputs the received echo signal as echo data to the controller 3.

Based on the echo data received from the probe 1, the controller 3 generates an image representing a carotid artery 6, for example, and also generates an improperly tilted positioning image representing how much the probe 1 is improperly tilted with respect to the carotid artery 6. In the following example, the carotid artery 6 is supposed to be an example of the region of interest (ROI).

The monitor 4 displays an image representing the carotid artery 6 and the improperly tilted positioning image that have been generated by the controller 3.

Figure 2:
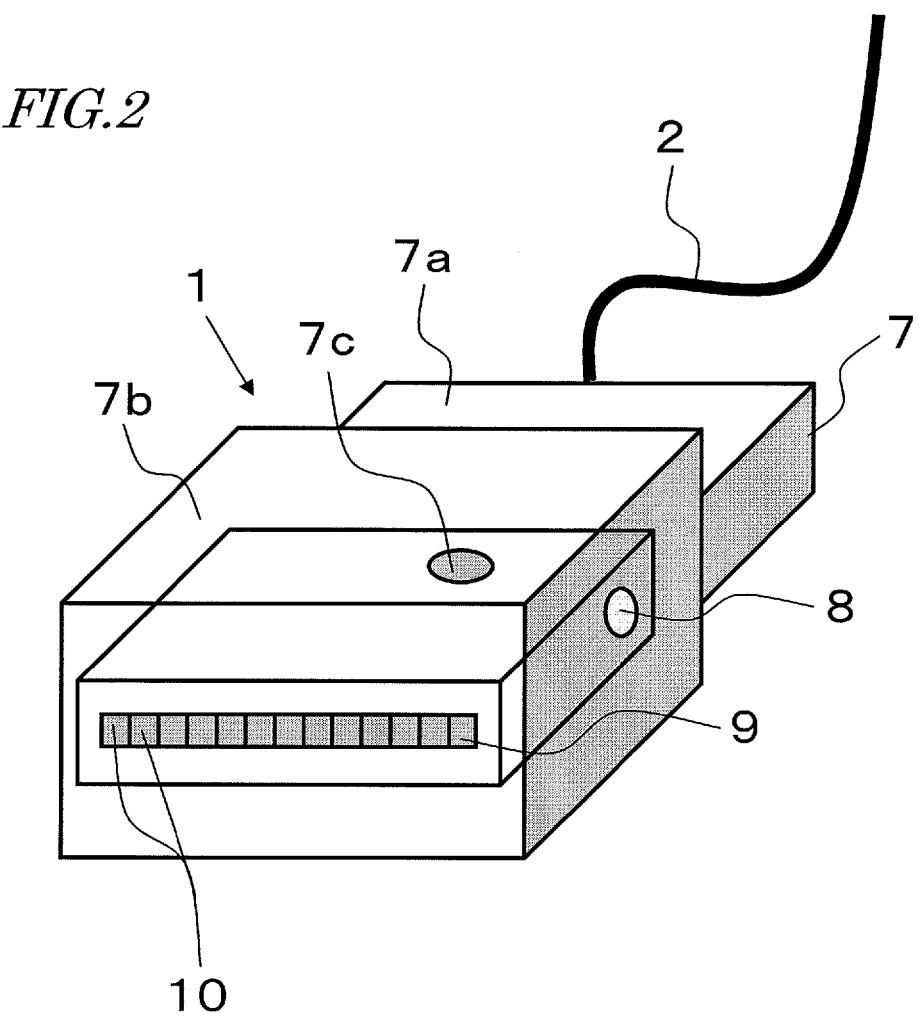
FIG. 2 is a perspective view generally illustrating the configuration of a probe 1.
Figure 3:
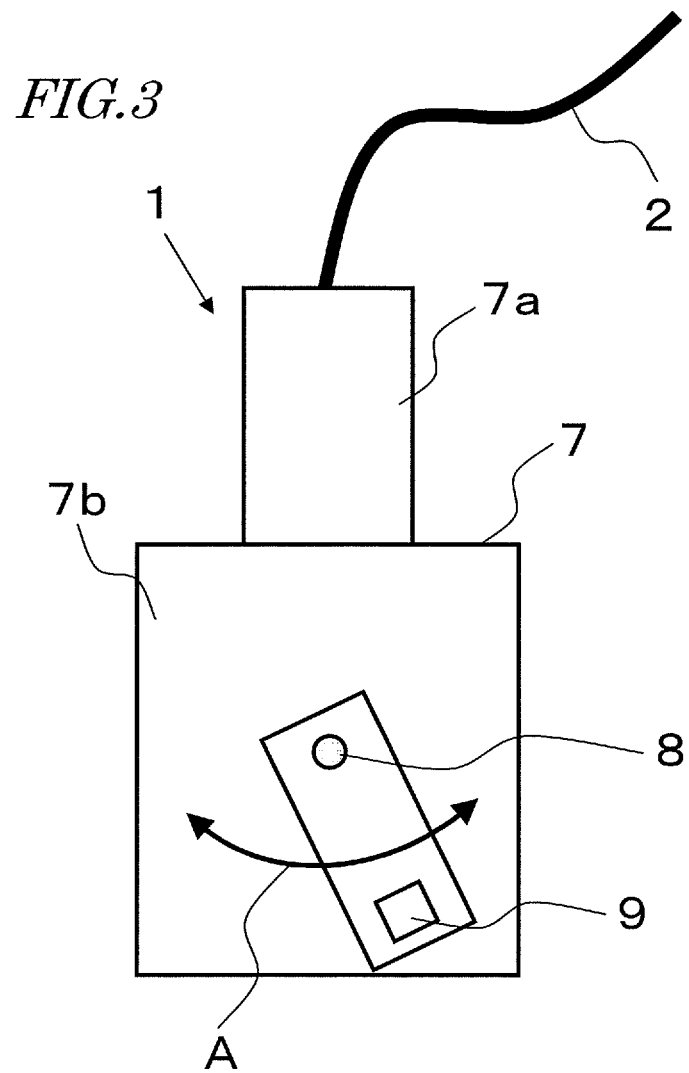
FIG. 3 is a cross section generally illustrating the configuration of the probe 1.

FIGS. 2 and 3 illustrate the configuration of the probe 1. At the front end inside of the body case 7 of the probe 1, arranged is an array 9 of transducers, which can swing freely on an axis 8 of swing.

Specifically, a portion of the body case 7, which is arranged closer to the cable 2, has a smaller size than the rest of the body case 7, and functions as a grip portion 7a, which allows the inspector to hold the probe 1 in his or her hand. The wider and bigger portion of the body case 7, which is arranged more distant from the cable 2, functions as a contact portion 7b to be brought into contact with the organism.

And as shown in FIGS. 2 and 3, a number of transducers are arranged in line in the long-axis direction at the front end of that contact portion 7b.

Although the transducers that form the array 9 are arranged in line in this example, the transducers may also be arranged in a curved pattern such as a convex or concave pattern or any other appropriate pattern.

In the array 9 of transducers, arranged are a number of ultrasonic transducers, which are made of a piezoelectric ceramic such as PZT (lead zirconate titanate), a piezoelectric single crystal such as PMN-PT (lead magnesium niobate-lead titanate) or a high molecular material such as PVDF (poly (vinylidene fluoride)), for example. The voltage applied to the respective piezoelectric bodies can be switched electrically with the controller 3.

The array 9 of transducers is formed by arranging a number of ultrasonic transducers 10 in line. By scanning the object with an ultrasonic beam with the array 9 of transducers swung on the axis of rotation 8 in the directions indicated by the arrow A shown in the cross-sectional view of FIG. 3, a detected image can be obtained from a wide range with a broad width.

As a method for scanning the object with an ultrasonic beam with the array 9 of transducers swung, a drive mechanism such as a motor may be used in general. Alternatively, a shape change layer, of which the material is deformed by an electric field (or voltage) applied, may be arranged on either the upper surface of the array 9 of transducers (i.e., one side of the array 9 that faces the subject) or the lower surface thereof (i.e., the other side of the array 9 that is opposite from that side that faces the subject), and may be deformed so as to scan the object with an ultrasonic beam. According to such a method, if the shape change layer is arranged on one side of the array 9 of transducers that faces the subject, for example, the ultrasonic beam is refracted by using a difference in sonic velocity between the ultrasonic beam that has come from the shape change layer and the ultrasonic beam that has come from the subject, thereby scanning the subject. On the other hand, if the shape change layer is arranged on the other side of the array 9 that is opposite from that side of the array 9 that faces the subject, then the shape change layer may be deformed, and the direction the array 9 faces may be changed, with the voltage applied, thereby scanning the subject with an ultrasonic beam. The principle of such a method will be described later as to a third specific preferred embodiment of the present invention. According to that method, the array 9 of transducers is arranged where the axis 8 of rotation is arranged in the example illustrated in FIG. 3.

The ultrasonic diagnostic apparatus 100 of this preferred embodiment has a positioning mode, in which the probe 1 needs to be positioned properly with respect to the carotid artery 6, and a detection mode, in which the specific status of the carotid artery 6 needs to be detected.

In the positioning mode, since a wide range, including a range where nobody knows whether the blood vessel can be detected at all, needs to be searched for the blood vessel, the swing angle of the array 9 of transducers as indicated by the arrow A is set to be a large angle. On the other hand, in the detection mode to be carried out after that, the detecting operation may be focused on a relatively small range almost along the blood vessel, which has been narrowed down to a certain degree in the positioning mode, and therefore, the swing angle of the array 9 may be smaller than the former swing angle by one digit or more. In this preferred embodiment, the swing angle is supposed to be 30 degrees in the positioning mode and only 1 degree in the detection mode to be carried out after that, as will be described in detail later.

Also, as shown in FIG. 2, a probe origin marker 7c is set on the contact portion 7b of the body case 7 at one end of the array 9 of transducers. By reference to the position of that probe origin marker 7c, the operator adjusts the position of the probe 1 as will also be described in detail later.

Figure 4:
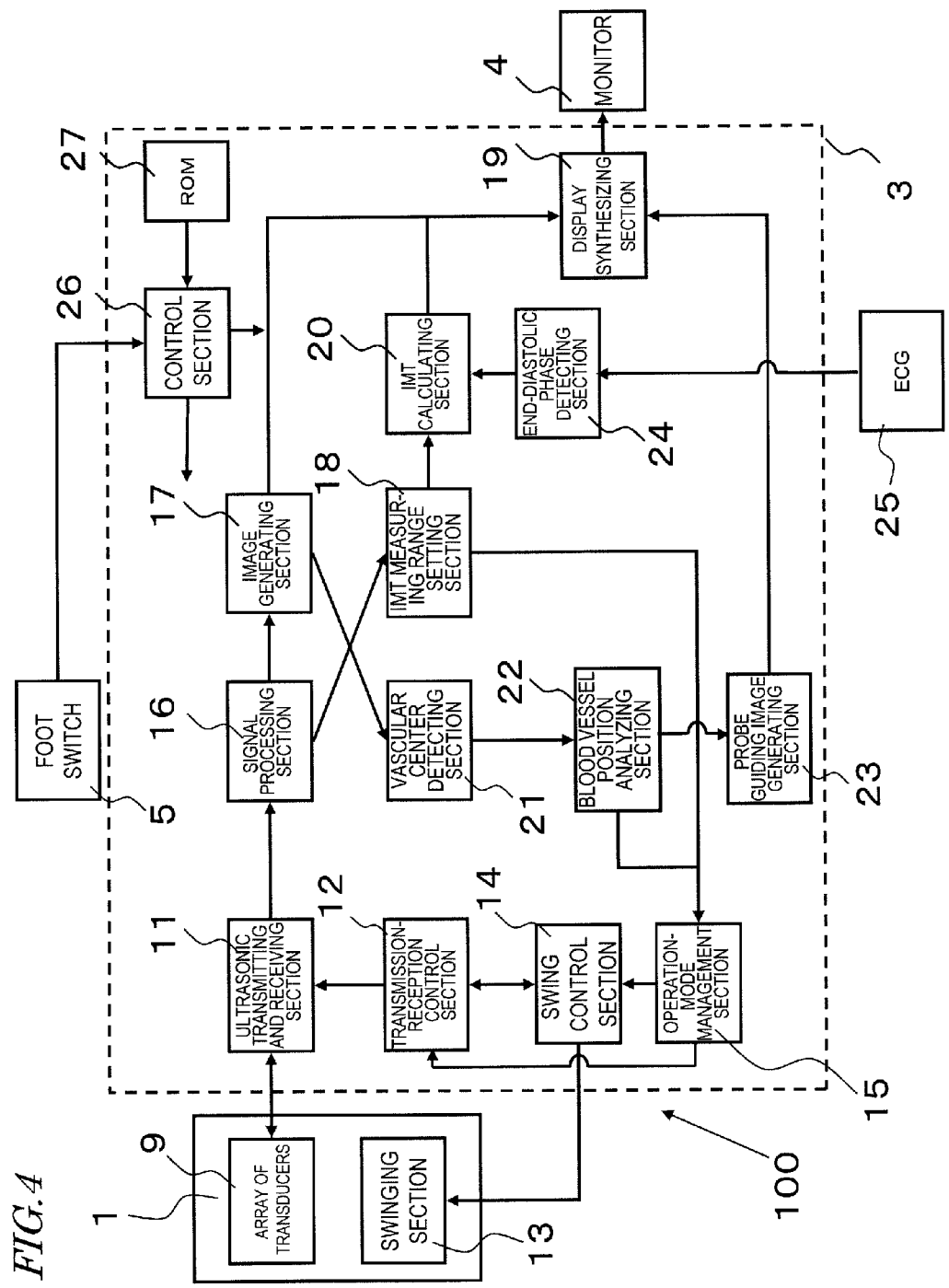
FIG. 4 is a block diagram illustrating the electrical configuration of the ultrasonic diagnostic apparatus 100.

FIG. 4 is a block diagram illustrating the electrical configuration of the ultrasonic diagnostic apparatus 100. An ultrasonic transmitting and receiving section 11 is connected to the array 9 of transducers of the probe 1. And a transmission-reception control section 12 is connected to the ultrasonic transmitting and receiving section 11.

Also, a swing control section 14 is connected to a swinging section 13, which swings the array 9 of transducers of the probe 1.

A mode of operation management section 15 is connected to the transmission-reception control section 12 and the swing control section 14. The mode of operation management section 15 gets the array of transducers 9 swung by the swinging section 13 ±15 degrees with respect to the center of swing (i.e., with an amplitude (swing angle) of 30 degrees) in the positioning mode described above and then swung by ±0.5 degrees with respect to the center of swing (i.e., with an amplitude (swing angle) of 1 degree) in the detection mode after that.

A signal processing section 16 is connected to the ultrasonic transmitting and receiving section 11. And an image generating section 17 and an IMT measuring range setting section 18 are connected in parallel to the signal processing section 16.

The monitor 4 is connected to the image generating section 17 by way of a display synthesizing section 19.

The display synthesizing section 19 is also connected to the IMT measuring range setting section 18 by way of an IMT calculating section 20.

A vascular center detecting section 21 is connected to the image generating section 17. The mode of operation management section 15 and a probe guiding image generating section 23 are connected to the vascular center detecting section 21 by way of a blood vessel position analyzing section 22. Among these sections, the probe guiding image generating section 23 is connected to the display synthesizing section 19.

On the other hand, an electrocardiogram (which will be abbreviated herein as "ECG") checking section 25 is connected to the IMT calculating section 20 by way of an end-diastolic phase detecting section 24.

It should be noted that the operations of these sections are controlled mainly by the control section 26, which is roughly made up of an ultrasonic transmitting and receiving section, a signal processing section and an image generating section and of which the program is stored in a ROM 27.

Also, the foot switch 5 described above may be connected as an input means to the control section 26. However, the foot switch 5 is just an example of the input means and any other input device may be connected as well.

Figure 5:
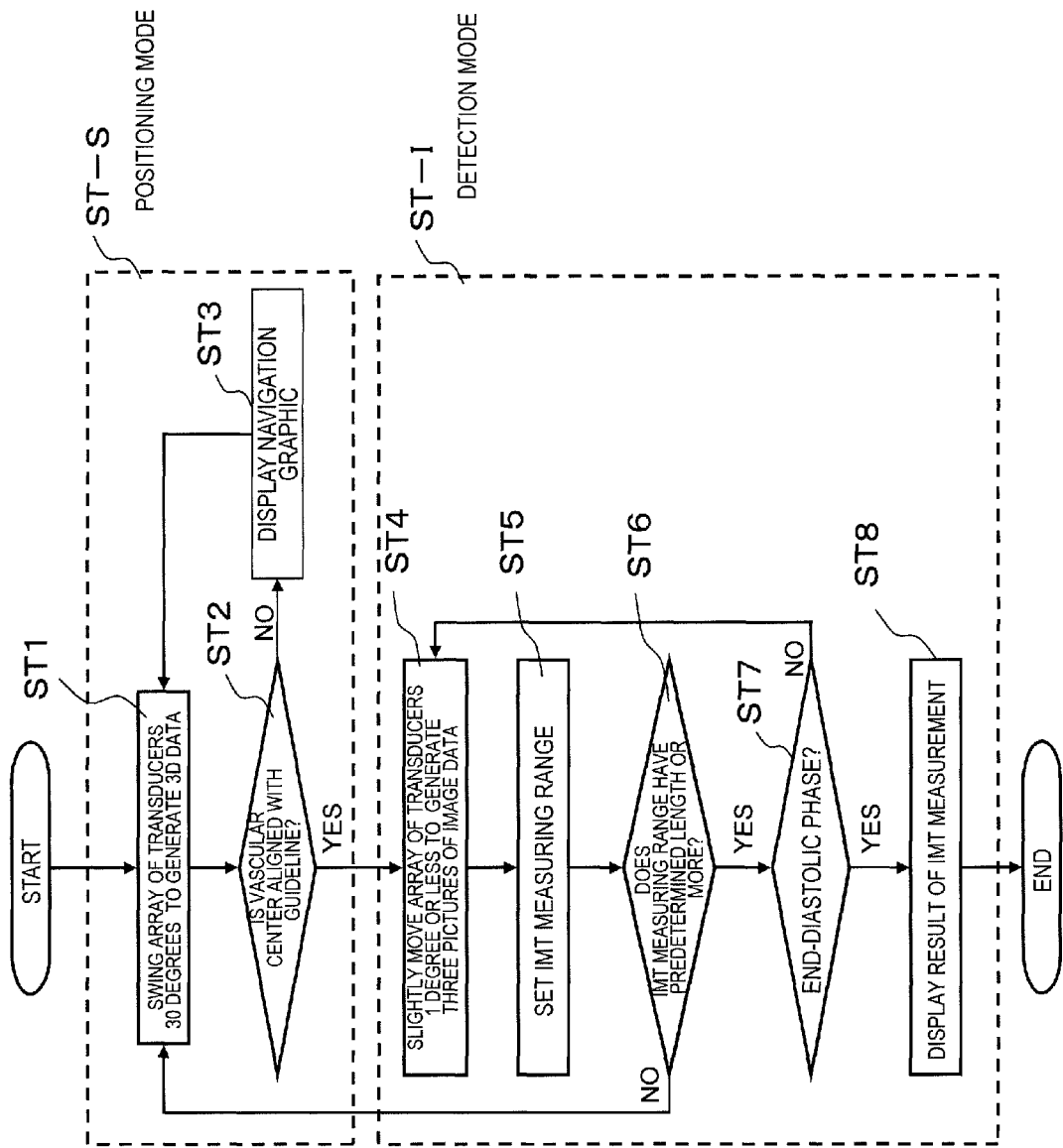
FIG. 5 is a flowchart showing the procedure of the processing to get done by the ultrasonic diagnostic apparatus 100.

FIG. 5 is a flowchart showing how to change the modes of operation from the positioning mode ST-S (where ST denotes "step" and the same abbreviation will be used in the rest of the description) into the detection mode ST-I. First of all, in the positioning mode ST-S, a linear array 9 of transducers is positioned so as to face, and be arranged parallel to, the carotid artery 6 that runs vertically through the subject's neck 28 as shown in FIG. 1. Nevertheless, as the direction in which the carotid artery 6 runs cannot be confirmed with the eyes, the array 9 of transducers does not have be positioned exactly parallel to the carotid artery 6. By performing this positioning operation, the array 9 of transducers can face the carotid artery 6 and can be arranged substantially parallel to the direction in which the carotid artery 6 runs.

Figure 6:
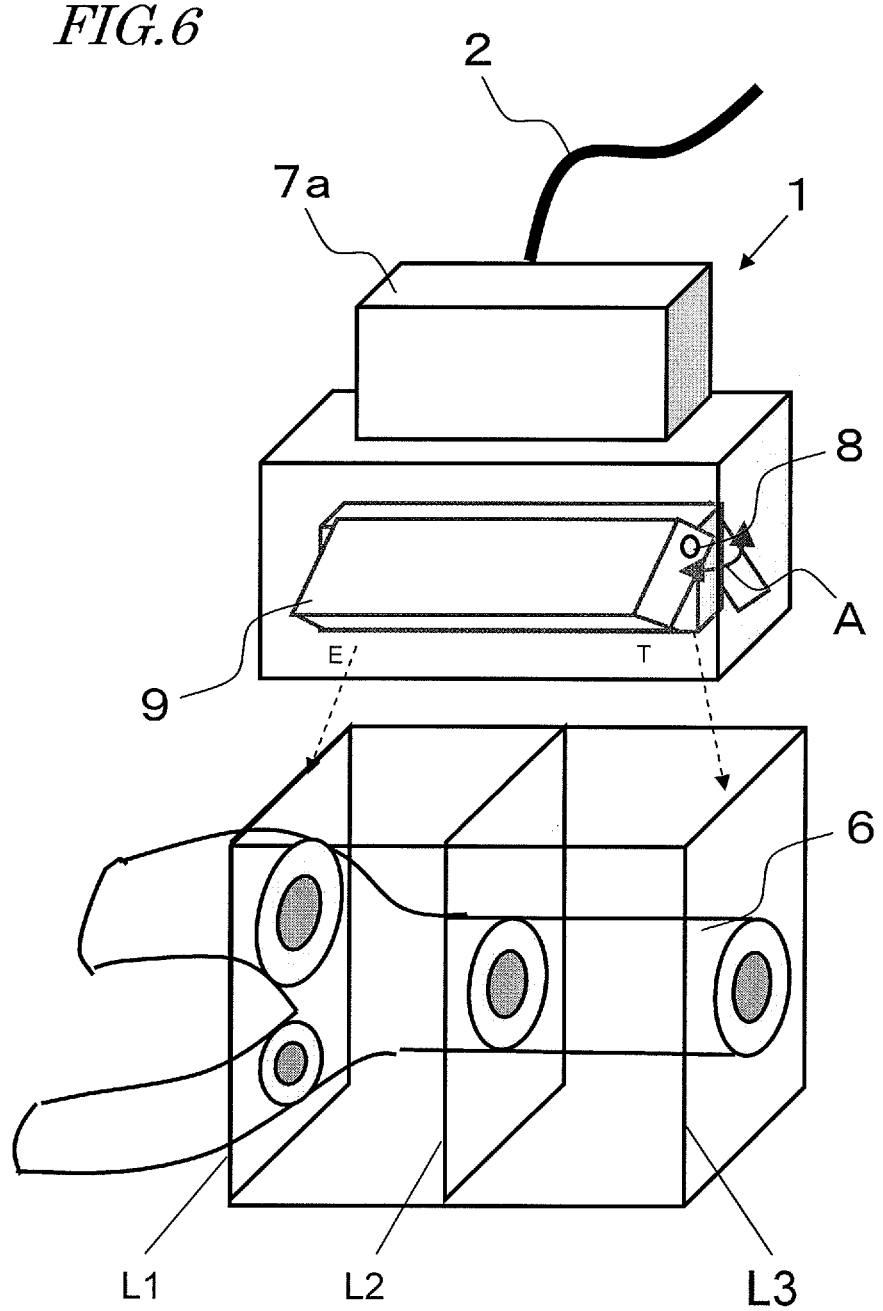
FIG. 6 is a perspective view illustrating how the probe 1 operates.
Figure 7:
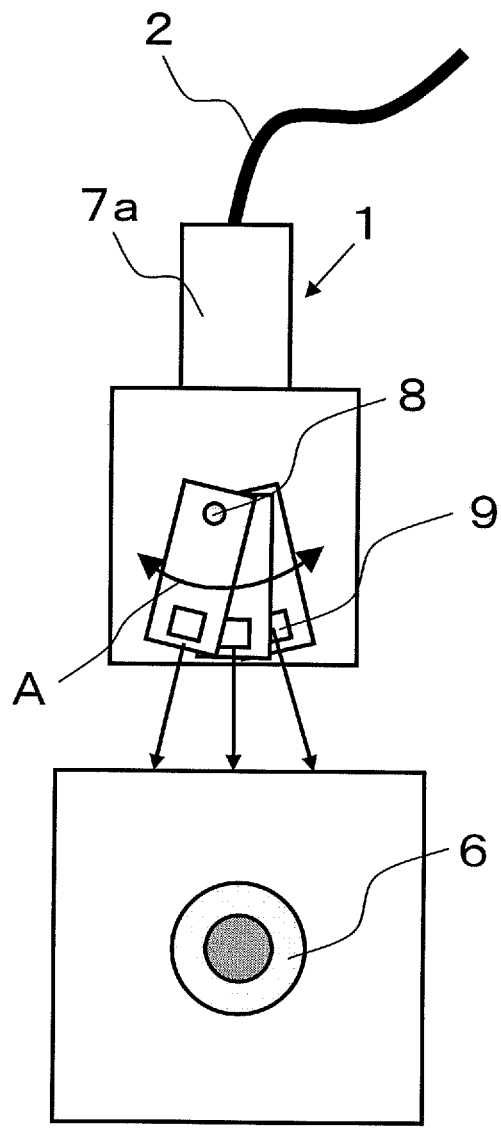
FIG. 7 is a side view illustrating how the probe 1 operates.

Thereafter, in accordance with the instruction to enter the positioning mode that has been given by the mode of operation management section 15 shown in FIG. 4, the swing control section 14 drives the swinging section 13. FIGS. 6 and 7 illustrate how the array 9 of transducers is swung. As indicated by the arrow A, the array 9 of transducers is swung on the axis of rotation 8 within a swing angle (i.e., a maximum angle of motion) of 30 degrees while sending out an ultrasonic beam at the same time. As a result, a detected image can be obtained from a wider range with an even broader width.

In this positioning mode ST-S, the swing angle (the maximum angle of motion) of the array 9 of transducers is set to be as large as 30 degrees. As a result, a stereoscopic (i.e., 3D) image representing the carotid artery 6 can be obtained as shown in FIG. 6 (in ST1 shown in FIG. 5).

In addition, not only such a stereoscopic image (3D image) but also shorter-axis cross sections L1, L2 and L3 of the neck 28 are obtained as shown in FIG. 6. These cross sections L1, L2 and L3 are obtained in this order downward along the neck 28.

Figure 8:
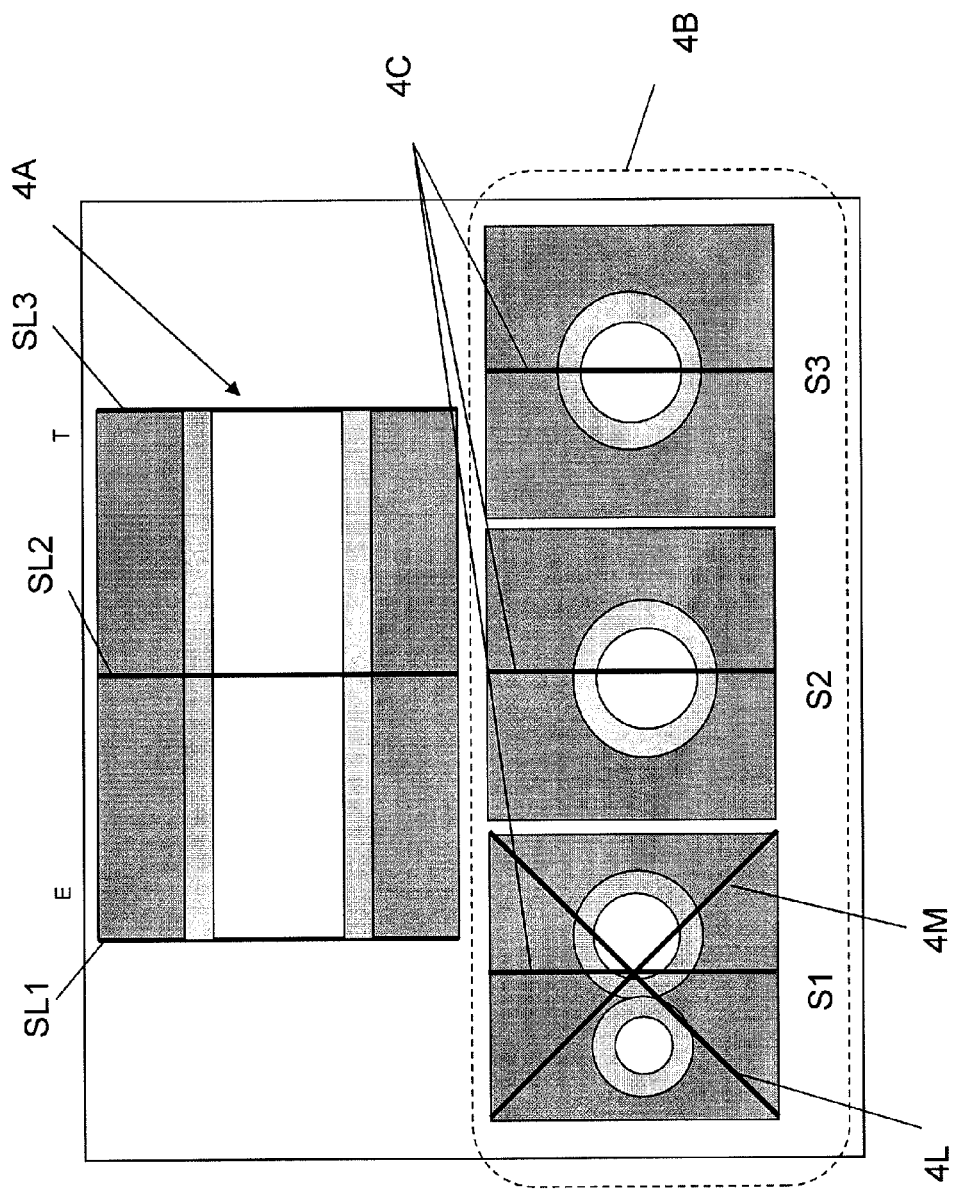
FIG. 8 illustrates what images may be displayed on the monitor 4.

FIG. 8 illustrates what may be displayed on the monitor 4. On the screen of the monitor 4, a long-axis image display area 4A is arranged in the upper half and a short-axis image display area 4B is arranged in the lower half.

One of important features to note in FIG. 8 is that in the short-axis tomographic image S1 as viewed on the short-axis cross section L1 shown in FIG. 6 and displayed in the short-axis image display area 4B, cross sections of two branches of the carotid artery, which run toward the top of the subject's head, appear as larger and smaller circles. That is to say, the short-axis tomographic image S1 shows a position where the carotid artery 6 branches into two.

That is to say, to stabilize the position for detection, the region of interest that has been set on the carotid artery 6 is defined to be as high as, and lower than, the branching point of the carotid artery 6.

As also shown in FIG. 8, probe contact angle guide lines 4L and 4M are drawn on the short-axis tomographic image S1. These probe contact angle guide lines 4L and 4M are lines, each of which forms an angle of 45 degrees with respect to the base of the short-axis tomographic image S1 (if the short-axis tomographic image S1 is displayed as a square image). The probe contact angle guide lines are sometimes called "probe insert angle guide lines". Over the branching point of the carotid artery, the relative positions of the two branches of the carotid artery on the short-axis tomographic image S1 change according to the angle of contact defined by the probe 1 with respect to the neck. For example, if the probe 1 is put on the neck so as to define an angle of contact of 90 degrees with respect to a virtual plane that covers the subject's nasal muscle, the cross sections of the two branches of the carotid artery will appear side by side as shown in FIG. 8. On the other hand, if the probe 1 is put on the neck with that angle of contact changed by 45 degrees toward the occipital region, then the cross sections of the two branches of the carotid artery will appear side by side substantially parallel to the probe contact angle guide line 4L. In this manner, the angle of contact defined by the probe 1 with respect to the neck can be known easily by these probe contact angle guide lines 4L and 4M.

On the other hand, as a centerline that runs through the short-axis tomographic images S2 and S3 that are respectively viewed on the short-axis cross sections L2 and L3 shown in FIG. 6 and displayed in the short-axis image display area 4B shown in FIG. 8, drawn is a blood vessel centering guide line 4C. By reference to this line, it can be seen on which side the center of the carotid artery 6 is now located and how much the center of the carotid artery 6 has shifted.

Unless the array 9 of transducers is parallel to the carotid artery 6, the IMP cannot be detected afterward. For that reason, the blood vessel centering guide line 4C is displayed to see if the array 9 of transducers is now arranged parallel to, and faces right to, the carotid artery 6. Hereinafter, it will be described how to generate the short-axis tomographic images S1 to S3 and how to find the center of the blood vessel.

As shown in FIG. 4, the information (echo data) that has been obtained from the array 9 of transducers is conveyed to the image generating section 17 by way of the ultrasonic transmitting and receiving section 11 and the signal processing section 16. In response to that signal, the image generating section 17 generates 3D image data, and the vascular center detecting section 21 calculates the center position of the blood vessel based on that 3D image data.

Specifically, by taking advantage of the fact that the carotid artery 6 has an almost circular cross section, the center position of the blood vessel is calculated based on the size of the circle and then compared to the blood vessel centering guide line 4C, thereby calculating the magnitude of shift between them. In the status shown in FIG. 8, cross sections of two branches of the carotid artery 6 appear in the short-axis tomographic image S1 and the center axis of the carotid artery 6 is aligned with the blood vessel centering guide line 4C that defines the centerline of the short-axis tomographic images S2 and S3. Consequently, it can be said that the probe 1 is now arranged at a right position for detection. It should be noted that the lines SL1, SL2 and SL3 shown in FIG. 8 indicate cross sections of the carotid artery 6 respectively corresponding to the short-axis cross sections L1, L2 and L3 shown in FIG. 6.

Figure 9:
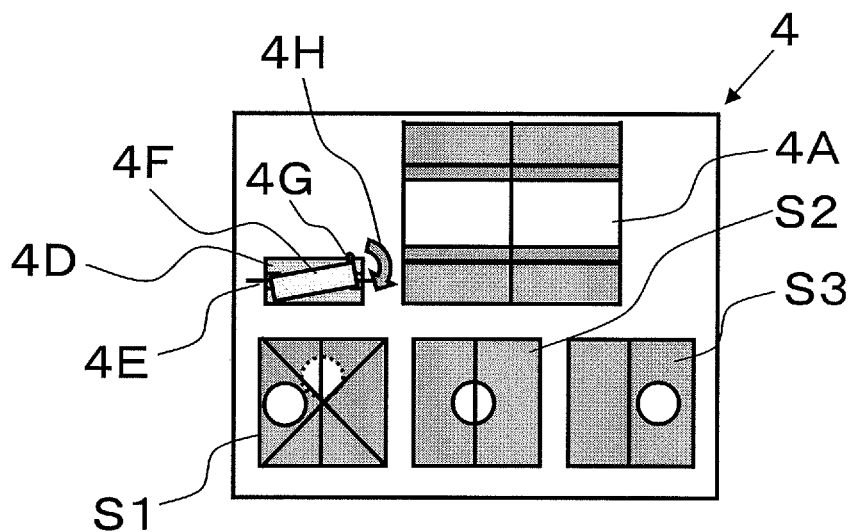
FIG. 9 illustrates a relative position of the probe 1 with respect to a carotid artery 6 and a symbol 4H prompting the operator to adjust the position of the probe 1 as displayed on the monitor 4.
Figure 10:
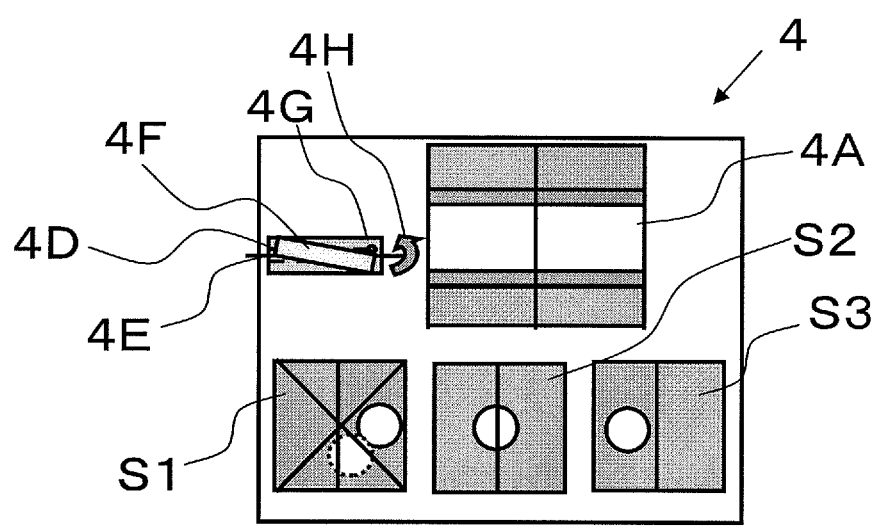
FIG. 10 illustrates another relative position of the probe 1 with respect to the carotid artery 6 and a symbol 4H prompting the operator to adjust the position of the probe 1 as displayed on the monitor 4.

FIGS. 9 and 10 illustrate relative positions of the probe 1 and the carotid artery 6, which are now displayed on the monitor 4, along with a symbol 4H that prompts the operator to change the position of the probe 1. In FIGS. 9 and 10, displayed are not only the short-axis tomographic images S1, S2 and S3 shown in FIG. 8 but also an improperly tilted positioning image 4D of the probe 1, which is displayed over the short-axis tomographic image S1.

This improperly tilted positioning image 4D not only indicates how much the probe 1 is now improperly tilted with respect to the carotid artery 6 but also prompts the operator to adjust the position of the probe 1 so that the probe 1 is arranged parallel to, and faces right to, the carotid artery 6.

More specifically, on the improperly tilted positioning image 4D, also shown are the centerline 4E representing the center axis of the carotid artery 6 (as the region of interest) to be detected by the probe 1 and a probe symbol 4F indicating how much the probe 1 is improperly tilted with respect to the centerline 4E. On the probe symbol 4F, further shown is a probe origin 4G.

The probe origin 4G is an image sign corresponding to the probe origin marker 7c that has been set at one end of the array of transducers 9 as shown in FIG. 1, and is displayed on the image on the monitor 4.

That is why if the arrow 4H of the probe symbol 4F of the improperly tilted positioning image 4D points downward as shown in FIG. 9, the operator may change the position of the probe 1 so that the probe origin marker 7c thereof moves in the direction indicated by that arrow 4H.

On the other hand, if the arrow 4H of the probe symbol 4F of the improperly tilted positioning image 4D points upward as shown in FIG. 10, the operator may change the position of the probe 1 so that the probe origin marker 7c thereof moves in the direction indicated by that arrow 4H.

Such an arrow 4H indicating in what direction the probe origin marker 7c of the probe 1 should be moved is generated by the vascular center detecting section 21, the blood vessel position analyzing section 22 and the probe guiding image generating section 23 shown in FIG. 4.

That is to say, the arrow 4H that prompts the operator to move the probe origin marker 7c of the probe 1 is generated by determining on which side of the blood vessel centering guide line 4C the carotid artery 6 is now located (and how much the carotid artery 6 is shifted) on the short-axis tomographic images S1, S2 and S3 shown in FIG. 8.

The respective image data representing the short-axis tomographic images S1, S2 and S3, the long-axis image display area 4A, the improperly tilted positioning image 4D, the centerline 4E, the probe symbol 4F, the probe origin 4G and the arrow 4H are all generated by the probe guiding image generating section 23 shown in FIG. 4. All of these image data are sent to the display synthesizing section 19 and synthesized therewith the image data in the long-axis image display area 4A that has been supplied from the image generating section 17. As a result, the images are displayed as shown in FIG. 9 or 10 (in ST2 and ST3 shown in FIG. 5).

As soon as it has been confirmed that the probe 1 has been put in a right position on the carotid artery 6 to detect the region of interest (i.e., when the arrow 4H shown in FIG. 9 or 10 disappears), the process advances to the detection mode ST-I shown in FIG. 5.

To enter the detection mode, the operator may tread on the foot switch 5 shown in FIG. 1, for example. Alternatively, as soon as the control section 26 senses that the arrow 4H has disappeared, the modes of operation may be automatically changed into the detection mode ST-I shown in FIG. 5, no matter whether a signal has been supplied from the foot switch 5 or not. It should be noted that the arrow 4H could either always have a constant size irrespective of the magnitude of shift or have its size changed according to the magnitude of shift so that the operator can see easily how much the probe 1 is still shifted.

Optionally, once it is confirmed that the probe 1 has been put at a right position on the carotid artery 6 to detect the region of interest, the operator may be notified of that not just by making the arrow 4H disappear as described above but also by changing some property of the display into what usually gives the operator an okay (or let's go) impression. For example, the display color of the improperly tilted positioning image 4D may be changed into green to indicate that status.

Figure 11:
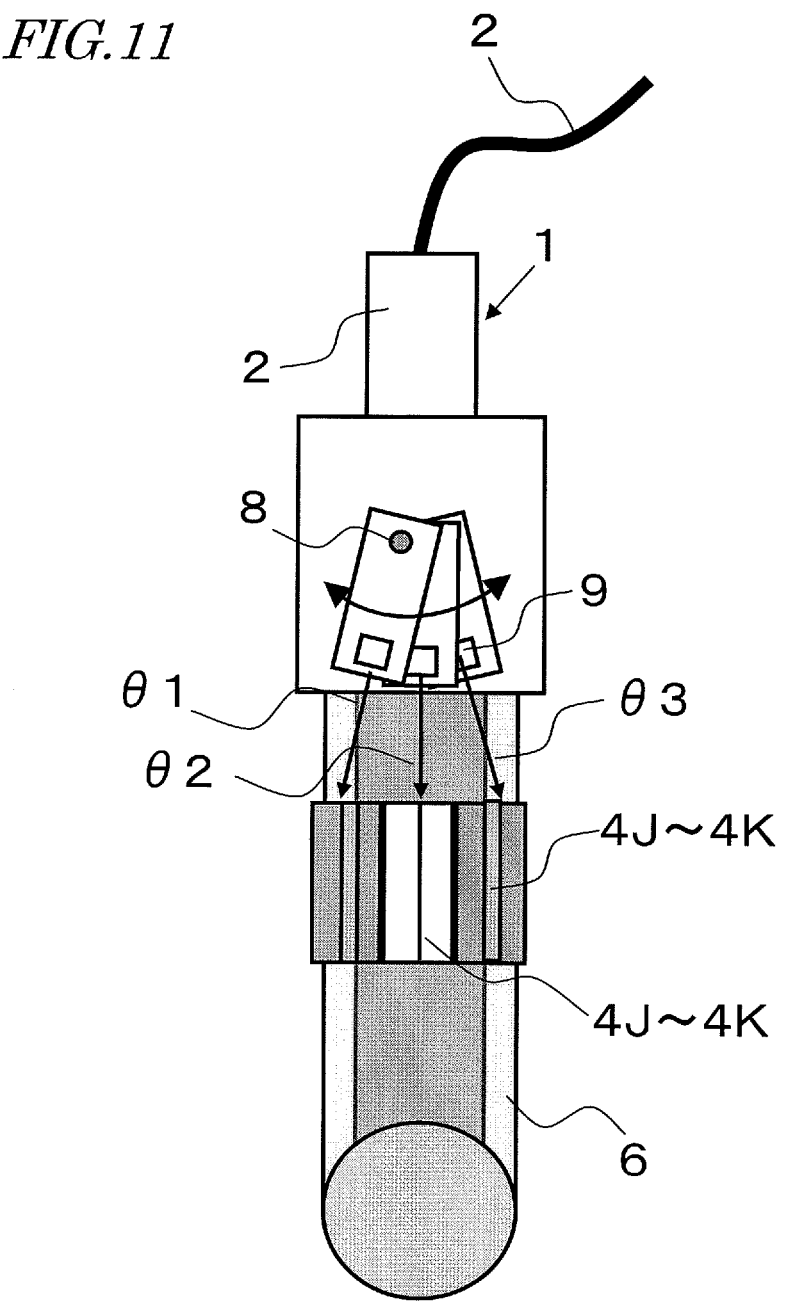
FIG. 11 is a side view schematically illustrating how the array 9 of transducers swings.

Next, in the detection mode ST-I shown in FIG. 5, in accordance with the instruction to enter the detection mode that has been given by the mode of operation management section 15 shown in FIG. 4, the swing control section 14 drives the swinging section 13. As a result, the swing control section 14 swings the array 9 of transducers on the axis of rotation 8 so that its swing angle (i.e., the maximum angle of motion) becomes as small as one degree as shown in FIG. 11. In this manner, the detection operation can be focused on only a very narrow range and targeted right on the carotid artery 6. More specifically, for that purpose, image data needs to be obtained from multiple points and an IMT value needs to be calculated (or measured) based on that image data.

Figure 12:
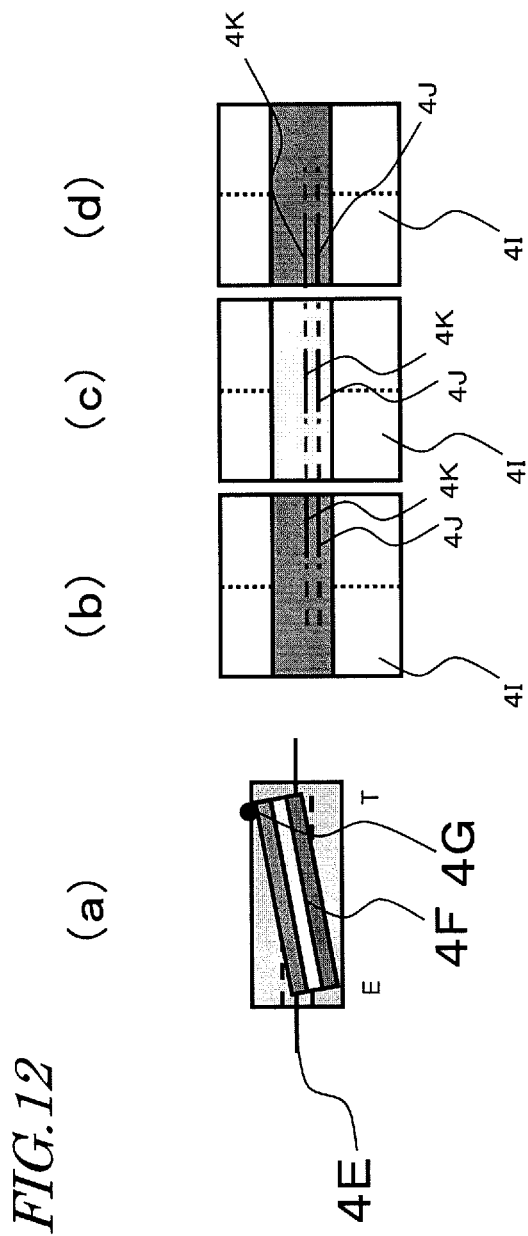
FIG. 12(a) illustrates a relative position of the probe with respect to the carotid artery.
FIGS. 12(b), 12(c) and 12(d) illustrate long-axis images Y1, Y2 and Y3 at swing angles θ1, θ2 and θ3, respectively.

As described above, the IMT measuring process is usually carried out on a portion of the carotid artery with a predetermined length and it is recommended that the IMT measuring range have a length of 1 cm. FIGS. 12 to 15 illustrate relative position of the array 9 of transducers with respect to the carotid artery 6. Specifically, FIG. 12(a) is an improperly tilted positioning image indicating their relative positions by using, in combination, a schematic representation illustrating a long-axis cross section of the carotid artery and a schematic representation illustrating a probe with the probe origin marker 4G. On the other hand, FIGS. 12(b) to 12(d) illustrate long-axis images Y1, Y2 and Y3 with swing angles θ1, θ2 and θ3, respectively. In each of these drawings, the lateral width represents a predetermined length of the carotid artery on which the IMT should be measured.

Figure 14:
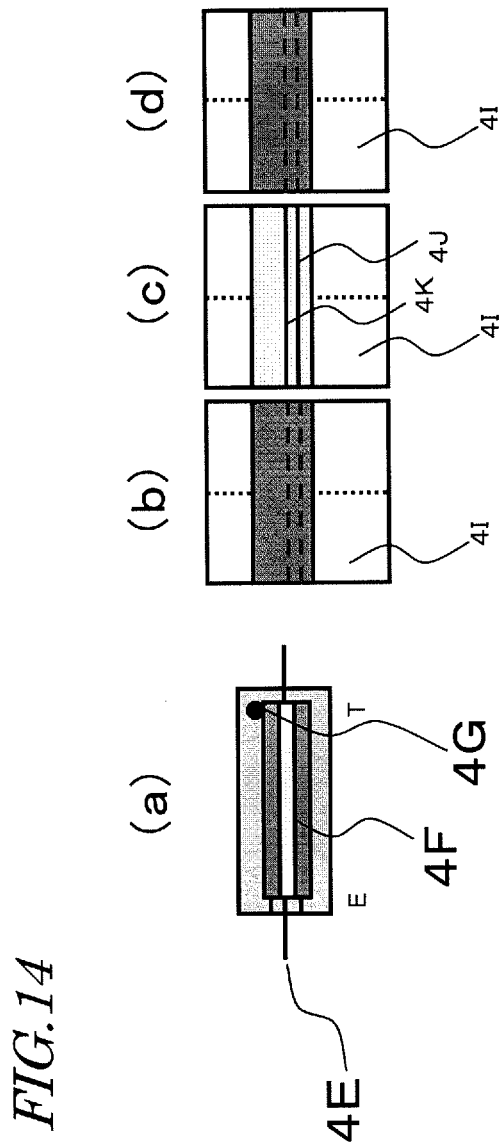
FIG. 14(a) illustrates still another relative position of the probe with respect to the carotid artery.
FIGS. 14(b), 14(c) and 14(d) illustrate long-axis images Y1, Y2 and Y3 at swing angles θ1, θ2 and θ3, respectively.

Among these drawings, FIG. 14 illustrates a state where the array 9 of transducers is arranged parallel to, and faces right to, the carotid artery 6. Specifically, FIG. 14(a) illustrates an ideal arrangement in which the centerline of the schematic representation illustrating a long-axis cross section of the carotid artery (i.e., the centerline 4E of the carotid artery 6) is aligned with that of the schematic representation illustrating the probe with the probe origin marker 4G. That is to say, FIG. 14(a) illustrates a state where the array 9 of transducers is put at a right position to get an IMT measured value.

If the ideal arrangement shown in FIG. 14(a) is realized, image data representing the IMT measurable range is included in a single picture of the image data so as to satisfy the predetermined length requirement (i.e., a media-adventitia boundary 4J and a lumen-intima boundary 4K are displayed clearly) as shown in FIG. 14(c) and as will be described later.

Figure 13:
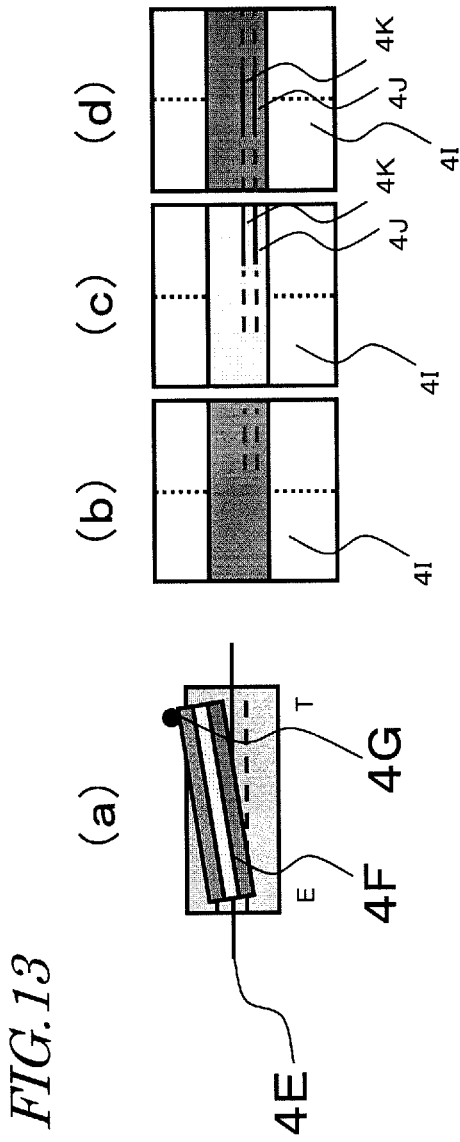
FIG. 13(a) illustrates another relative position of the probe with respect to the carotid artery.
FIGS. 13(b), 13(c) and 13(d) illustrate long-axis images Y1, Y2 and Y3 at swing angles θ1, θ2 and θ3, respectively.
Figure 15:
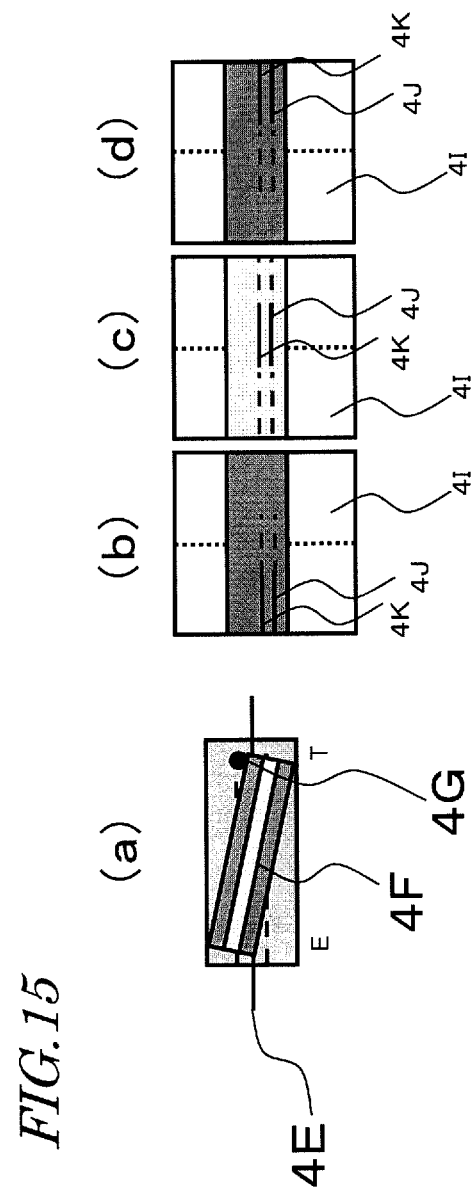
FIG. 15(a) illustrates yet another relative position of the probe with respect to the carotid artery.
FIGS. 15(b), 15(c) and 15(d) illustrate long-axis images Y1, Y2 and Y3 at swing angles θ1, θ2 and θ3, respectively.

Meanwhile, FIGS. 12 and 13 illustrate an improperly tilted state in which a portion of the array 9 of transducers with the probe origin 4G has shifted outward with respect to the centerline 4E representing the center axis of the carotid artery 6. On the other hand, FIG. 15 illustrates an improperly tilted state in which a portion of the array 9 of transducers with the probe origin 4G has shifted toward the centerline 4E of the carotid artery 6. In any of these states, the image data representing the IMT measurable range is included in a single picture of image data but fails to satisfy the predetermined length requirement.

That is why if the portion of the array 9 of transducers with the probe origin 4G has shifted either outward or inward with respect to the centerline 4E of the carotid artery 6 as shown in FIGS. 12, 13 and 15, naturally the probe 1 should be moved and aligned with the centerline 4E, Actually, however, since it is a very delicate fine adjustment to arrange the probe 1 parallel to such a thin object as the carotid artery 6, it is rather difficult for an unskilled person to get such a troublesome job done.

That is why according to this preferred embodiment, the ultrasonic diagnostic apparatus is designed so as to get the IMT detection (or measurement) done not just when the array 9 of transducers is arranged exactly parallel to the carotid artery 6 as shown in FIG. 14 but also even if the portion of the array 9 of transducers with the probe origin 4G is slightly tilted either outward as shown in FIG. 12 with respect to the centerline 4E of the carotid artery 6 or toward that centerline 4E.

This point will be described in further detail. Each of FIGS. 12(b), 13(b), 14(b) and 15(b) illustrates a long-axis image Y1 at the swing angle θ1 shown in FIG. 11. Each of FIGS. 12(c), 13(c), 14(c) and 15(c) illustrates a long-axis image Y2 at the swing angle θ2 shown in FIG. 11. And each of FIGS. 12(d), 13(d), 14(d) and 15(d) illustrates a long-axis image Y3 at the swing angle θ3 shown in FIG. 11 (in ST4 shown in FIG. 5).

Also, in portions (b) through (d) of FIGS. 12 to 15, 4I denotes the outside portion of the carotid artery 6, 4J denotes the media-adventitia boundary, 4K denotes the lumen-intima boundary, the dashed line indicates that neither the media-adventitia boundary nor the lumen-intima boundary can be rendered clearly based on the echo data, and the solid line indicates that both the media-adventitia and lumen-intima boundaries can be rendered clearly. There is an intima-media complex between the media-adventitia and lumen-intima boundaries 4J and 4K and the thickness of the intima-media complex (i.e., the thickness of the region between the media-adventitia and lumen-intima boundaries 4J and 4K) becomes the IMT value. That is why to detect the IMT value based on those portions (b) through (d) of FIGS. 12 to 15, it is important that the media-adventitia and lumen-intima boundaries 4J and 4K are caught definitely (i.e., rendered clearly) in those portions (b) through (d) of FIGS. 12 to 15.

Thus, the media-adventitia and lumen-intima boundaries 4J and 4K are caught definitely as a whole in those portions (b) through (d) of FIGS. 12, 14 and 15 not just when the array 9 of transducers is arranged exactly parallel to the carotid artery 6 as shown in FIG. 14 but also even if the portion of the array 9 of transducers with the probe origin 4G is slightly tilted either outward as shown in FIG. 12 with respect to the centerline 4E of the carotid artery 6 or toward that centerline 4E.

More specifically, in FIG. 12, the media-adventitia and lumen-intima boundaries 4J and 4K are caught definitely in a right-hand-side portion of FIG. 12(b), a central portion of FIG. 12(c) and a left-hand-side portion of FIG. 12(d). That is why it can be said that the image (data) indicating that the media-adventitia and lumen-intima boundaries 4J and 4K are caught definitely is rendering clearly a portion where a measured value can be obtained. Consequently, such an image will be an appropriate image for measuring the IMT. If the three images shown in FIGS. 12(b), 12(c) and 12(d) are used in combination, the region between the media-adventitia and lumen-intima boundaries 4J and 4K can be located with a predetermined length represented as a whole by overlapping the three images shown in FIGS. 12(b), 12(c) and 12(d) with each other (i.e., the lateral width in each of these drawings in this example), the media-adventitia and lumen-intima boundaries can be detected, and the thickness between them can be measured. As a result, the IMT value can be detected.

Also, in FIG. 14, the region between the media-adventitia and lumen-intima boundaries 4J and 4K can be located easily in the entire image shown in FIG. 14(c) (i.e., from its left end through its right end), and therefore, the IMT value can be detected. Furthermore, in FIG. 15, the media-adventitia and lumen-intima boundaries 4J and 4K are caught definitely in a left-hand-side portion of FIG. 15(b), a central portion of FIG. 15(c) and a right-hand-side portion of FIG. 15(d). Thus, combining these three image portions shown in FIGS. 15(b), 15(c) and 15(d) with each other, the region between the media-adventitia and lumen-intima boundaries 4J and 4K can be located as a whole and the IMT value can be detected. On the other hand, in FIG. 13, neither the media-adventitia boundary 4J nor the lumen-intima boundary 4K is caught clearly in FIG. 13(b) but the media-adventitia and lumen-intima boundaries 4J and 4K are caught clearly only in a right-hand-side portion shown in FIG. 13(c) and in a central portion shown in FIG. 13(d). That is why even if those image portions shown in FIGS. 13(b), 13(c) and 13(d) are combined with each other, the region between the media-adventitia and lumen-intima boundaries 4J and 4K cannot be located and the IMT value cannot be detected as a result.

As shown in FIG. 11, the media-adventitia and lumen-intima boundaries 4J and 4K are rendered clearly around the center axis of the carotid artery 6. Specifically, when the array 9 of transducers has a swing angle θ2, a single fine line indicates, in the overlapping square shown right under its arrow, that the media-adventitia boundary 4J and the lumen-intima boundary 4K are rendered clearly. In FIG. 11, also shown, by a certain width of shift between the media-adventitia and lumen-intima boundaries 4J and 4K, is that the media-adventitia and lumen-intima boundaries 4J and 4K are rendered unclearly in the outside portion of the carotid artery 6 when the array 9 has a swing angle θ1 or θ3. The image shows that those boundaries are not rendered clearly unlike what is indicated by the single fine line when the swing angle is θ2.

Figure 16:
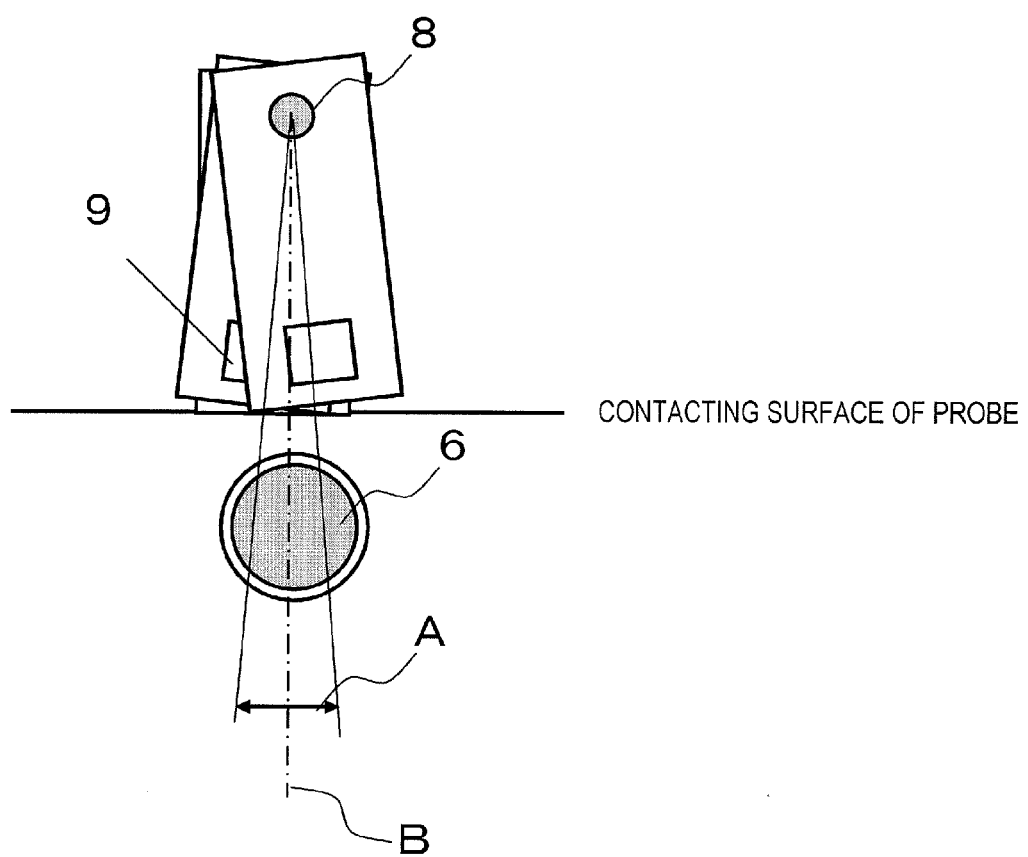
FIG. 16 is a side view illustrating a relative position of the probe with respect to the carotid artery.

FIGS. 16 and 17 show that this ultrasonic diagnostic apparatus is designed so as to detect the IMT value even if the portion of the array 9 of transducers with the probe origin 4G is slightly tilted either outward as shown in FIG. 12 with respect to the centerline 4E of the carotid artery 6 or toward that centerline 4E. The IMT can naturally be detected when the array 9 of transducers is arranged parallel to, and faces right to, the carotid artery 6 as shown in FIG. 14. In this detection mode ST-I, the array 9 of transducers swings on the axis 8 of rotation so as to form a swing angle (i.e., maximum angle of motion) of only one degree and the detecting operation can be focused on such a very narrow range and targeted only on the carotid artery 6 as described above.

In this case, the IMT detectible range A and a position B where the media-adventitia and lumen-intima boundaries 4J and 4K can be detected clearly are shown in FIG. 16. FIG. 17(a) illustrates an improperly tilted state in which the portion of the array 9 of transducers with the probe origin 4G is slightly tilted outward with respect to the centerline 4E representing the center axis of the carotid artery 6. FIG. 17(b) illustrates a specific detection position C that falls within not only a predetermined length defined by the image data representing the measured value retrievable region (i.e., appropriate image data) to detect the IMT at that time but also the detectible range (width) A.

As in FIG. 16, the width A shown in FIG. 17(b) indicates the IMT detectible range and the line B indicates the position where the media-adventitia and lumen-intima boundaries 4J and 4K can be detected clearly.

That is to say, in FIG. 17(b), in the improperly tilted state in which the portion of the array 9 of transducers with the probe origin 4G is slightly tilted outward as shown in FIG. 12 with respect to the centerline 4E of the carotid artery 6, the array 9 of transducers subtly moves on the axis 8 of rotation so as to form a swing angle (i.e., maximum angle of motion) of only one degree. That is why only while passing through the width A defining the IMT detectible range (but in a still improperly tilted state in this case), the region between the media-adventitia and lumen-intima boundaries 4J and 4K can be detected clearly as shown in FIG. 12 (in ST5 and ST6 shown in FIG. 5).

In this preferred embodiment, the range of the image data representing the measured value retrievable region to detect the IMT (i.e., appropriate image) is supposed to have a predetermined length D of 1 cm as shown in FIG. 17(b).

That is to say, to locate the region between the media-adventitia and lumen-intima boundaries 4J and 4K described above, the range should have a length of at least 1 cm. And if this condition is satisfied (i.e., if the sum of the lateral widths of the three portions as indicated by the three slants C in FIG. 17(b) can be at least equal to 1 cm), the IMT can be detected from the region of interest (i.e., the carotid artery 6 in this example) by measuring (or calculating) the maximum thickness (max IMT) or mean thickness (mean IMT) based on the IMT detected values of the respective positions.

Now take a look at FIG. 4 again.

The IMT measuring range setting section 18 determines which of the regions shown in portions (b) through (d) of FIGS. 12 to 15 should be used as the measuring range. Also, if the region between the media-adventitia and lumen-intima boundaries 4J and 4K can be located within the 1 cm range as described above, the IMT measuring range setting section 18 passes the IMT data, which is a value detected at the positions indicated by the slants C in FIG. 17(b), to the IMT calculating section 20.

The electrocardiogram (which will be abbreviated herein as "ECG") checking section 25 is connected to the IMT calculating section 20 by way of the end-diastolic phase detecting section 24. In the end-diastolic phase that has been detected by the end-diastolic phase detecting section 24, the IMT is detected and displayed on the monitor 4 after having been processed by the display synthesizing section 19 (in ST7 and ST8 shown in FIG. 5).

As a result, according to this preferred embodiment, the IMT can be detected (or measured) not just when the array 9 of transducers is arranged exactly parallel to the carotid artery 6 but also even if the portion of the array 9 of transducers with the probe origin 4G is slightly tilted either outward as shown in FIG. 12 with respect to the centerline 4E of the carotid artery 6 or toward that centerline 4E. Consequently, the measuring work can be simplified significantly.

As can be seen from the foregoing description, with the ultrasonic diagnostic apparatus 100 of this preferred embodiment, even an unskilled person can get the IMT detection done both easily and accurately.

In the preferred embodiment described above, images detected from multiple points are supposed to be displayed in the detection mode as shown in FIGS. 12 to 15. However, those images shown in FIGS. 12 to 15 do not always have to be displayed. Rather as long as the range where the region between the media-adventitia and lumen-intima boundaries 4J and 4K (i.e., the range of the image data representing the measured value retrievable region) can be located and that has a length of at least 1 cm can be secured within a predetermined amount of time after the modes of operation have been changed into the detection mode, the IMT can also be calculated even without any images. In that case, if the minimum required length (representing the IMT measuring range) cannot be secured even after a predetermined amount of time, then the modes of operation will be changed into the positioning mode again as shown in the flowchart of FIG. 5 to attempt to position the probe 1 more properly with respect to the carotid artery 6.

Also, if the user is not a skilled person but can still perform the carotid artery rendering operation fairly well, then he or she may use only the detection mode and may determine whether or not the carotid artery can be rendered roughly without using the positioning mode.

Furthermore, in the preferred embodiment described above, the IMT is supposed to be measured when that range in which the region between media-adventitia and lumen-intima boundaries 4J and 4K can be located has a length of 1 cm. However, the predetermined length does not always have to be 1 cm. Alternatively, the decision can also be made by seeing if the length of that range accounts for at least a predetermined percentage of 1 cm. The higher that percentage, the more proper the IMT measuring range and the more accurate the IMT measured value can be. On the other hand, if the percentage is set to be low, then the IMT measurement can also get done even if the probe has somewhat shifted from a proper position, and therefore, the operability can be increased.

Furthermore, in the preferred embodiment described above, the IMT is supposed to be measured using images. However, the IMT can also be measured using echo data yet to be transformed into the images.

Furthermore, in the preferred embodiment described above, short-axis tomographic images are supposed to be obtained by swinging the array of transducers that are arranged in line. However, the same processing can also be carried out with an additional array of transducers arranged perpendicularly to one or multiple arrays of transducers that are arranged in line(s).

Furthermore, in the preferred embodiment described above, the region of interest is supposed to be the carotid artery and its IMT is supposed to be measured. However, this is just an example of the present invention. For instance, the present invention is also applicable for use to measure the IMT of the femoral artery. Alternatively, the technique of the present invention can also be used with an image that renders clearly the anterior and posterior walls of the blood vessel defined to be an appropriate one when the vascular diameter of the abdominal artery is measured.

Furthermore, even when an embryo is measured, the technique of the present invention can also be used with an image that renders clearly a measuring site such as a thigh bone defined as an appropriate image.

Embodiment 2

Figure 18:
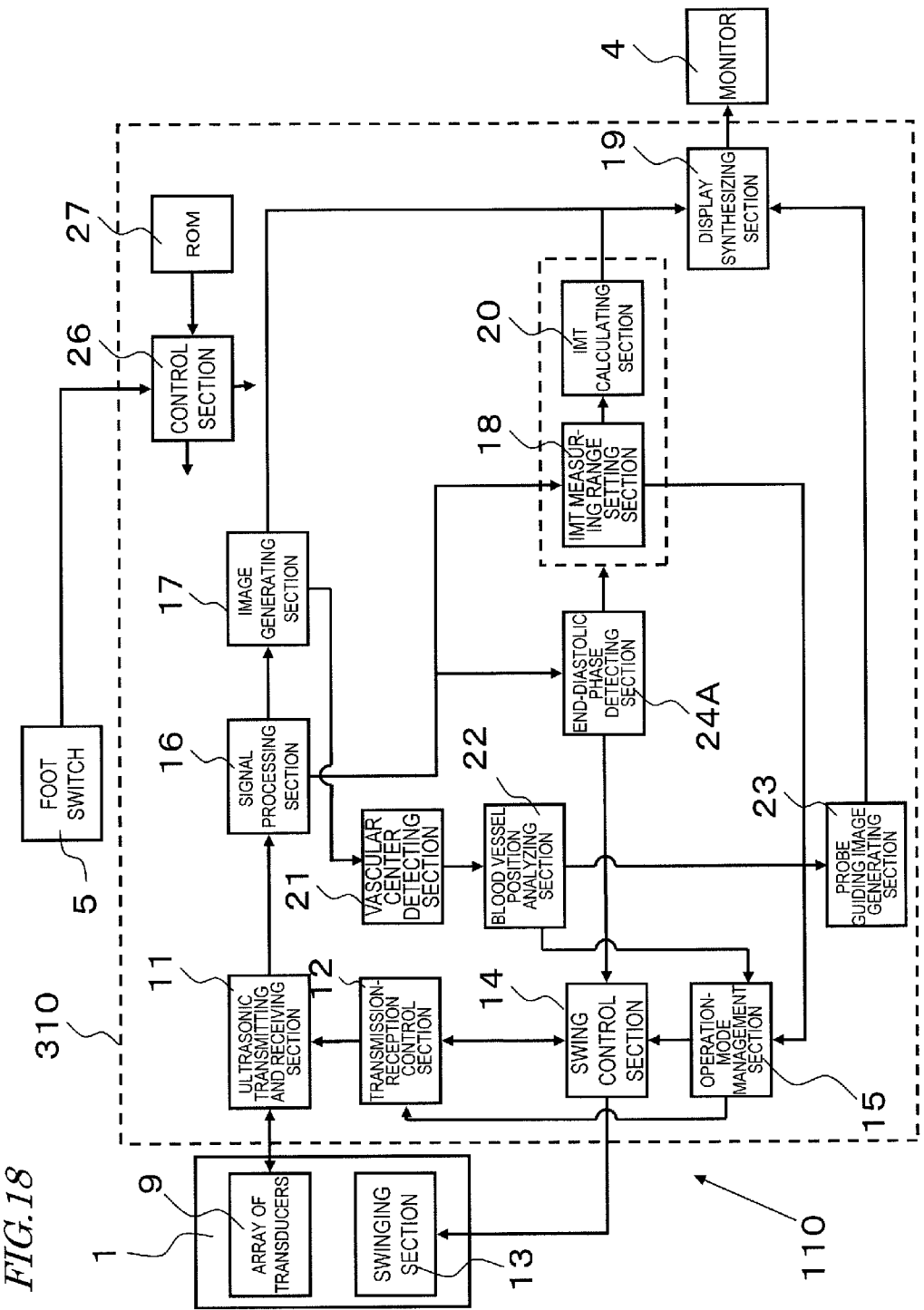
FIG. 18 is a block diagram illustrating the electrical configuration of an ultrasonic diagnostic apparatus 110 as a second preferred embodiment of the present invention.

FIG. 18 is a block diagram illustrating the electrical configuration of an ultrasonic diagnostic apparatus 110 as a second specific preferred embodiment of the present invention. The ultrasonic diagnostic apparatus 110 includes the probe 1, a controller 310, the monitor 4, and the foot switch 5.

In the ultrasonic diagnostic apparatus 110 shown in FIG. 18, any component also included in the ultrasonic diagnostic apparatus 100 of the first preferred embodiment and having substantially the same function as its counterpart is identified by the same reference numeral and its description will be omitted herein.

As shown in FIG. 18, the ultrasonic diagnostic apparatus of this preferred embodiment includes an end-diastolic phase detecting section 24A instead of the end-diastolic phase detecting section 24 and ECG checking section 25 of the first preferred embodiment shown in FIG. 4.

The end-diastolic phase detecting section 24A also detects the end of a vascular systolic phase by the technique disclosed in Japanese Patent No. 4189405 and further detects the IMT at that timing. The entire disclosure of Japanese Patent No. 4189405, including all of its description and drawings, is hereby incorporated by reference.

Specifically, the end-diastolic phase detecting section 24A includes a tissue tracking section, which analyzes the signal received from the signal processing section 26 to track the motion of the subject's tissue, and a feature quantity detecting section, which detects a feature quantity representing the motion of the subject's tissue to track and outputs a feature quantity detection signal. The tissue tracking section tracks the motion of the vascular wall of the carotid artery. The IMT value is ideally measured when the vascular wall has the maximum thickness. The carotid artery rapidly dilates in the systolic phase and contracts slowly in the diastolic phase. The feature quantity detecting section tracks such motion of the vascular wall of the carotid artery and detects the end of the diastolic phase when the vascular wall has the maximum thickness.

With such a configuration adopted, there is no need to attach the electrocardiogram (which will be abbreviated herein as "ECG") checking section 25 to the subject, and therefore, it becomes even easier for an unskilled person to get the IMT detection (or measurement) done properly.

Figure 19:
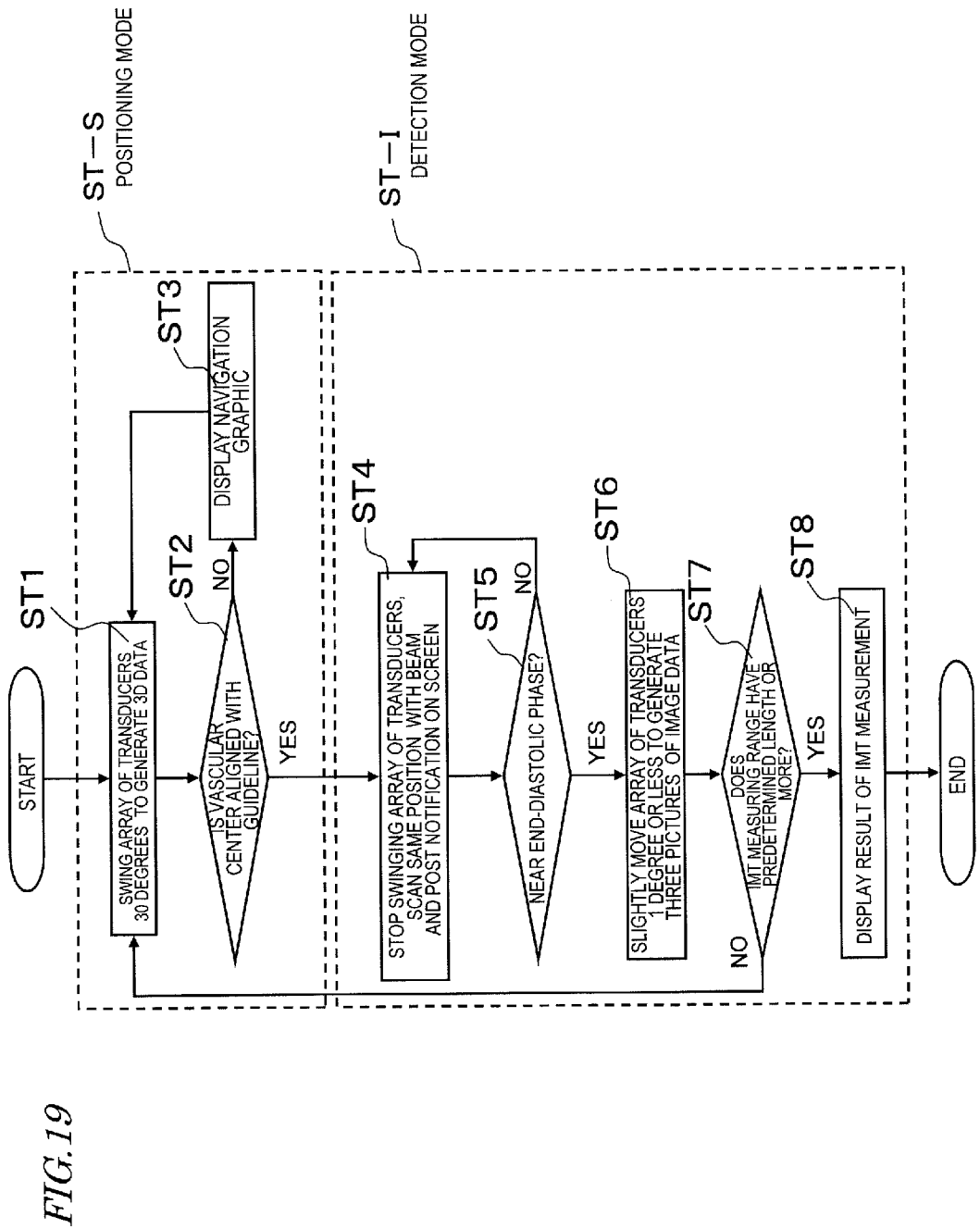
FIG. 19 is a flowchart showing the procedure of the processing to get done by the ultrasonic diagnostic apparatus 110.

In this preferred embodiment, when the center of the carotid artery 6 is either aligned with, or sufficiently close to, the centerline 4E, the swing of the array 9 of transducers is stopped, the same region of the carotid artery 6 is irradiated with a beam in that state, and the image representing that region (such as the one shown in FIG. 8) is displayed on the monitor 4 as in ST4 shown in FIG. 19.

Then, the end of the diastolic phase is detected in ST5. The images shown in FIGS. 12 to 15 are generated in ST6 as in ST4 shown in FIG. 5. Next, in ST7, it is determined whether or not the IMT measuring range has at least a predetermined length as in ST6 shown in FIG. 5. And the INT value is displayed on the monitor 4 in ST8.

Embodiment 3

Figure 20A:
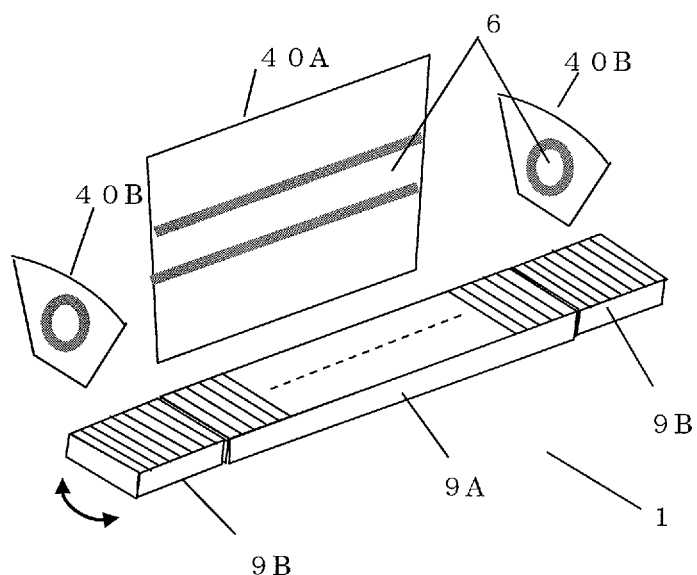
FIG. 20A is a perspective view generally illustrating an arrangement of the probe 1 according to a third preferred embodiment of the present invention.

FIG. 20A illustrates a probe 1 according to a third preferred embodiment of the present invention. The probe 1 is connected to the ultrasonic diagnostic apparatus of the first or second preferred embodiment described above, and subjected to an ultrasonic beam transmission and reception control by the ultrasonic diagnostic apparatus so as to receive an echo signal. Then, the echo signal thus received is transmitted as echo data to the ultrasonic diagnostic apparatus. As a result, an ultrasonic diagnostic image can be obtained.

In the arrays 9A and 9B of transducers of this preferred embodiment, also arranged are a number of ultrasonic transducers, which are made of a piezoelectric ceramic such as PZT (lead zirconate titanate), a piezoelectric single crystal such as PMN-PT (lead magnesium niobate-lead titanate) or a high molecular material such as PVDF (poly(vinylidene fluoride)), for example. The voltage applied to the respective piezoelectric bodies can be switched electrically with the controller 3, thereby obtaining ultrasonic diagnostic images.

The array 9A of transducers to be arranged to face the carotid artery 6 scans the object with an ultrasonic beam in the long-axis direction, thereby obtaining echo data in the long-axis direction, which will be used afterward in the processing step of displaying a long-axis image with a circuit. On the other hand, the arrays 9B of transducers scan the object with an ultrasonic beam in a short-axis direction, which intersects with the long-axis image display direction at substantially right angles, thereby obtaining short-axis echo data, which will be used afterward in the processing step of displaying a short-axis image with a circuit.

In this case, the echo data that has been obtained by the array 9A of transducers is transformed into an ultrasonic image by a known electronic control method. On the other hand, the arrays 9B of transducers need to scan the object with an ultrasonic beam in the short-axis direction to generate an image. Examples of such methods of scanning the object with an ultrasonic beam in the short-axis direction include mechanically rotating or reciprocating the arrays 9B of transducers using a motor, for example. Another method is providing a material to be deformed with an electric field (or voltage) applied to either the upper surface of the arrays 9B of transducers that faces the subject or the lower surface thereof that is opposite from the former surface and scanning the object with an ultrasonic beam with that material deformed. The latter method will be described in detail later.

Figure 20B:
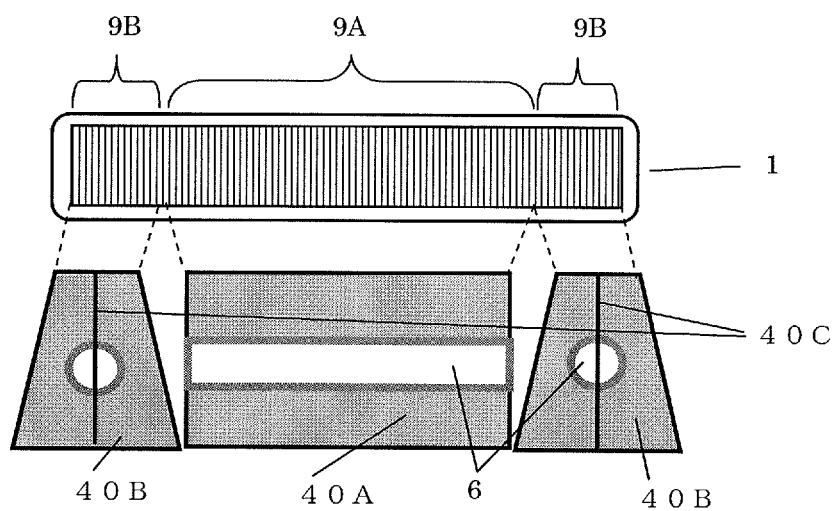
FIG. 20B illustrates how the array of transducers of the probe 1 are associated according to the third preferred embodiment with images in the positioning mode.
Figure 20C:
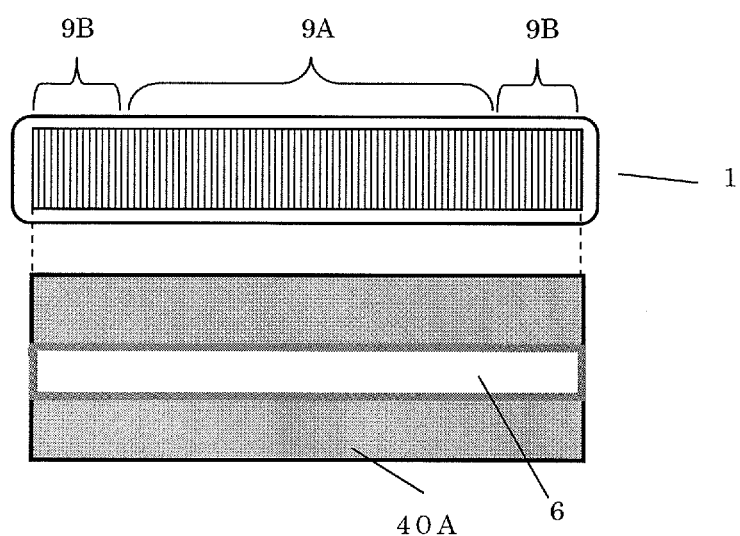
FIG. 20C is a perspective view generally illustrating how the array of transducers of the probe 1 are associated according to the third preferred embodiment with images in the detection mode.

Suppose the operator has put the probe 1 on the subject substantially parallel to his or her carotid artery 6. Then, as shown in FIGS. 20A to 20C, when an ultrasonic beam is transmitted from, or received at, the array 9A of transducers, an ultrasonic tomographic image 40A is displayed based on the echo data obtained. In the meantime, the arrays 9B of transducers are physically rotated, reciprocated or swung perpendicularly to the direction in which the transducers are arranged in the array 9A and scan the object with the ultrasonic beam while being moved physically that way. And ultrasonic tomographic images 40B are displayed based on the echo data thus obtained. In the example illustrated in FIGS. 20A through 20C, the arrays 9B of transducers are supposed to be arranged at both ends of the array 9A of transducers. With such an arrangement adopted, the operator can align the probe 1 with the vascular center axis of the carotid artery 6 more easily while monitoring the ultrasonic images 40B at both ends. FIG. 20A schematically illustrates those arrays of transducers and ultrasonic images as a perspective view to make their arrangement easily understandable. Actually, however, those arrays 9A and 9B of transducers of the probe 1 and the images displayed 40A and 40B are associated with each other as shown in FIG. 20B.

An actual method for measuring the IMT with the modes of operation changed into the detection mode after the probe has been positioned in the positioning mode will be described with reference to FIGS. 20B and 20C.

FIG. 20B illustrates a status in the positioning mode, in which the operator positions the probe 1 so that the centers of the arrays 9A and 9B of transducers of the probe 1 are aligned with the vascular center axis of the carotid artery 6.

The positioning may be carried out in the following manner. Specifically, ultrasonic images 4B (i.e., positioning images) are obtained by scanning the object with an ultrasonic beam with the motions of the arrays 9B of transducers at both ends physically controlled in the short-axis direction, while the long-axis ultrasonic image 4A is also obtained by the array 9A of transducers. As a result, a tomographic image representing the carotid artery 6 is obtained. In that case, however, the centerline of the tomographic image is not always aligned with, but often shifted from, the vascular center axis of the carotid artery 6. Thus, the operator makes fine adjustment so as to reduce that shift from the vascular center axis of the carotid artery 6 by moving the probe 1 so that the vascular center axis is aligned with the blood vessel centering guide lines 4C of the ultrasonic images 4B (as positioning images). When the vascular center axis is aligned with the blood vessel centering guide lines 4C of the ultrasonic images 4B (as positioning images), the center axis of the blood vessel in the long-axis direction is displayed on the ultrasonic image 4A. As the positioning mode ends in such a state, the modes of operation are changed into the detection mode. It should be noted that the modes of operation may be changed from the positioning mode into the detection mode by any arbitrary method. For example, by providing the function of automatically sensing that the vascular center axis gets aligned with the blood vessel centering guidelines 4C of the ultrasonic images 4B, the modes of operation may be changed into the detection mode automatically. Alternatively, by providing a selector switch for any part of the apparatus and by turning the switch manually, the modes of operation may be changed into the detection mode.

FIG. 20C illustrates what images may be displayed in the detection mode. In the detection mode, the arrays 9B of transducers that have been used in the positioning mode are returned to their original positions where the arrays 9B have the same array direction and the same short-axis tilt direction as the array 9A of transducers. Then, echo data is obtained by operating both of these arrays 9A and 9B of transducers in combination and a long-axis ultrasonic image 4A (i.e., detected image) is generated and displayed. In this manner, the long-axis ultrasonic image 4A (detected image) can present a broader (or longer) area than the ultrasonic image 4A shown in FIG. 20B does. Particularly when the carotid artery 6 is inspected, its branched portions that lead to the brain (corresponding to what is identified by L1 in FIG. 6, for example) are located around the subject's lower jaw. That is why as described in Japanese Patent No. 4237256, those two arrays of transducers that are arranged at both ends for positioning purposes cannot display an image in the long-axis direction. For that reason, the branched portions of the blood vessel sometimes may not be displayed and may generate a dead space, which could pose a problem in making a diagnosis. However, such a problem can be overcome by using the ultrasonic probe of this preferred embodiment.

As described above, by performing these series of processing steps with the modes of operation changed from the positioning mode into the detection mode, even an unskilled person can measure the IMT with good reproducibility and with high accuracy in an ultrasonic image 4A that covers a wide range.

In the preferred embodiment described above, two positioning images are supposed to be obtained from two regions by the two arrays 9B of transducers that are arranged at both ends. However, three or more positioning images may be obtained from three or more regions by arrays of transducers that are arranged at both ends and at the center, for example. In that case, positioning may also be carried out by getting the positioning images displayed selectively by some of the arrays of transducers. Still alternatively, in the positioning mode, the long-axis image 4A does not have to be displayed but three or more positioning images alone may be displayed to carry out positioning. And when the modes of operation are changed into the detection mode, only the long-axis image may be displayed. Even so, the same effect can also be achieved.

Next, another exemplary method for scanning the object with an ultrasonic beam in the short-axis direction by using the arrays 9B of transducers will be described with reference to FIG. 21. Specifically, according to that method, the object is scanned with an ultrasonic beam by providing a material to be deformed with an electric field applied either on the upper surface of the arrays 9B of transducers (that faces the subject) or on the lower surface thereof (that is opposite from the former surface of the arrays 9B of transducers) and by deforming that material.

Figure 21:
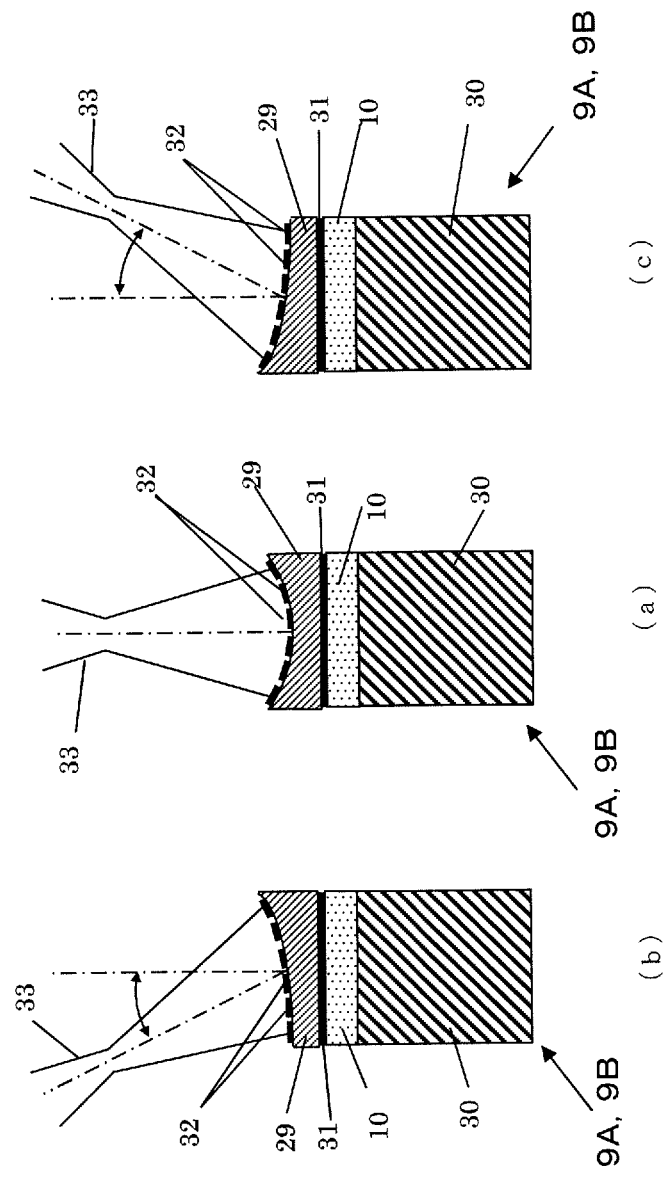
FIG. 21 shows cross-sectional views generally illustrating a method for transmitting an ultrasonic wave from a part of an array of transducers.

FIG. 21 illustrates generally cross sections of the arrays 9A and 9B of transducers shown in FIGS. 20A to 20C as viewed on a plane that intersects with the array direction at right angles. Each of these arrays 9A and 9B of transducers includes an ultrasonic transducer 10, a shape change layer 29, a back loading member 30 that supports the ultrasonic transducer 10, and electrodes 31 and 32, which are arranged on the upper and lower surfaces of the shape change layer 29 to scan the object with an ultrasonic beam. In order to transmit an ultrasonic beam using these arrays 9A and 9B of transducers, actually a variable power supply for applying an electrical signal should be arranged between the electrodes 31 and 32 but its illustration is omitted in FIG. 21.

The electrodes 31 and 32 that sandwich the shape change layer 29 are located in the regions of the arrays 9B of transducers shown in FIGS. 20A to 20C.

The ultrasonic transducer 10 may be made of a piezoelectric ceramic such as PZT, a piezoelectric single crystal such as PMN-PT or a composite piezoelectric material as a composite of a material and a high molecular material.

Although not shown, a grounded electrode and a signal electrode are respectively arranged in front of, and behind, the ultrasonic transducer 10 in the thickness direction. The shape change layer 29 is arranged in front of the ultrasonic transducer 10 in the thickness direction so as to face the subject and has the function of changing the direction of an ultrasonic beam.

While being transmitted through the shape change layer 29, the ultrasonic beam should have a different sonic velocity from while being reflected and returning from the subject. By using such a difference in sonic velocity effectively, the shape change layer 29 changes the direction of the ultrasonic beam.

Furthermore, the shape change layer 29 of this preferred embodiment has a curved surface opposed to the subject so as to converge the ultrasonic beam at an arbitrary depth in the subject. It will be described in further detail what difference this feature makes.

If the ultrasonic beam 33 should go straight on and then be converged at an arbitrary depth as shown in FIG. 21(*a*), that surface of the shape change layer 29 that is opposed to the subject may have such a shape with a single radius of curvature. The ultrasonic beam can be converged by turning the surface shape of the shape change layer 29 into either a concave shape or a convex one depending on the magnitude of the difference in sonic velocity between the shape change layer 29 and the subject. For example, if the ultrasonic beam is transmitted at a lower sonic velocity through the shape change layer 29 than the subject, the shape change layer 29 should have a convex surface in order to converge the ultrasonic beam. Conversely, if the ultrasonic beam is transmitted at a higher sonic velocity through the shape change layer 29 than the subject, the shape change layer 29 should have a concave surface.

On the other hand, if the ultrasonic beam 33 should have its traveling direction changed (into the one that intersects at right angles with the array direction of the arrays 9B of transducers shown in FIGS. 20A through 20C in this example) and be converged at an arbitrary depth as shown in FIGS. 21(*b*) and 21(*c*), then the curved surface of the shape change layer 29 that is opposed to the subject may have such a shape, of which the radius of curvature varies gradually from one position to another.

That surface of the shape change layer 29 that is opposed to the subject can be changed by dividing one of the two electrodes (e.g., the electrode 32 in this example) of the shape change layer 29 into multiple pieces and by controlling the voltages that are applied as electrical signals to those pieces of the electrode. In order to control the depth of focus and traveling direction of the ultrasonic beam by changing the shape of the shape change layer 29 in this manner, the shape should be changed with high accuracy. For that purpose, the number of pieces of the electrode 32 should be increased and the shapes of those pieces of the electrode 32 and the voltages applied to them should also be controlled precisely.

This shape change layer 29 may be made of an ionic conductive high molecular polymer, a dielectric polymer, a conductive polymer or any other high molecular material to be deformed with an electrical signal applied thereto.

The ionic conductive high molecular polymer is a polymer actuator including an ion exchange resin and two electrodes that sandwich the resin between them. The polymer actuator has the function of deforming the high molecular material by causing ions in the ion exchange resin to move with an applied voltage and swelling a portion of the material to which the ions have moved. Examples of such polymer actuators include high molecular materials in which a functional group such as a sulfonate group or a carboxyl group has been introduced into polyethylene, polystyrene, a or fluorine resin and high molecular materials including a non-conductive high molecular material such as polyvinylchloride (PVC), polymethylmethacrylate (PMMA) or polyurethane and an ionic substance.

On the other hand, if the dielectric polymer is sandwiched between two electrodes and if a voltage is applied between the electrodes, the dielectric polymer is deformed by being compressed in the thickness direction and expanded in the plane direction due to the electrostatic attraction produced between the electrode. Examples of such dielectric polymers include silicone rubber, polyurethane and acrylic elastomer.

Furthermore, if electric terminals are extended from the conductive polymer and if a voltage is applied between the electric terminals, then the conductive polymer between the electric terminals will shrink. On the other hand, if the applied voltage is removed, then the conductive polymer recovers its original shape. As such a conductive polymer, a polypyrrole resin may be used, for example.

These are just examples of materials that can be used in the present invention. Thus, any other polymer material can also be used as long as it can be deformed with an electrical signal applied.

For example, if the ionic conductive high molecular polymer is used as a material for the shape change layer 29, the voltage applied between the electrodes 31 and 32 causes ions to move to a portion of the material and to swell that portion, thereby deforming the high molecular material to varying degrees. That is why by changing the voltage to apply between those electrodes 31 and 32, respective portions of the shape change layer 29 on those pieces of the electrode 32 can be deformed to varying degrees. As a result, that surface of the shape change layer 29 that is opposed to the subject can have its shape changed arbitrarily and the object can be scanned with an ultrasonic beam that has traveled perpendicularly to the arrays 9A and 9B of transducers. Consequently, ultrasonic images in the short-axis direction can be obtained.

In the preferred embodiment described above, the shape change layer is supposed to be arranged on one side of the ultrasonic transducer 10 that faces the subject. Optionally, another shape change layer may be arranged either between the ultrasonic transducer 10 and the back loading member or behind the back loading member. In that case, the object may be scanned with an ultrasonic beam with the arrays 9B of transducers of the ultrasonic transducer 10 physically deformed by controlling the voltage applied to the shape change layer. Even so, the same effect can also be achieved.

Embodiment 4

In the first and second preferred embodiments of the present invention described above, multiple tomographic images of the region of interest are captured by moving (i.e., swinging) a single array 9 of transducers to the right and left as shown in FIGS. 2 and 3. Meanwhile, a fourth specific preferred embodiment of the present invention to be described below is a method for measuring the IMT using a probe in which two more arrays 9C and 9E of transducers are arranged on both sides of a single array 9D of transducers.

Figure 22:
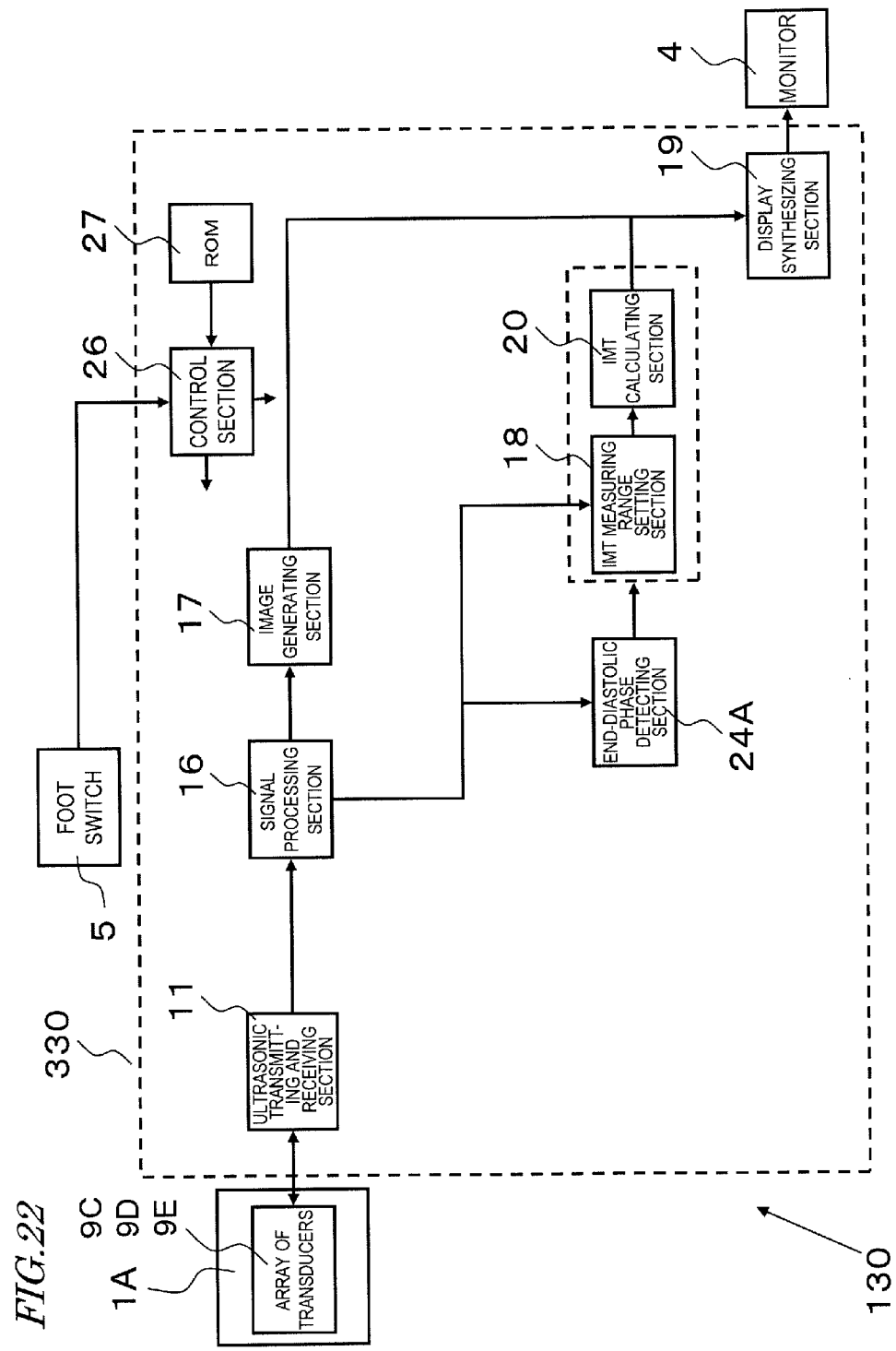
FIG. 22 is a block diagram illustrating the electrical configuration of an ultrasonic diagnostic apparatus 130 as a fourth preferred embodiment of the present invention.

FIG. 22 is a block diagram illustrating the electrical configuration of an ultrasonic diagnostic apparatus 130 as a fourth specific preferred embodiment of the present invention. The ultrasonic diagnostic apparatus 130 includes a probe 1A, a controller 330, the monitor 4, and the foot switch 5. As shown in FIG. 22, the ultrasonic transmitting and receiving section 11 is connected to the arrays 9C, 9D and 9E of transducers of the probe LA.

In the ultrasonic diagnostic apparatus 130 shown in FIG. 22, any component also included in the ultrasonic diagnostic apparatus 100 or 110 of the first or second preferred embodiment and having substantially the same function as its counterpart is identified by the same reference numeral and its description will be omitted herein.

Figure 23:
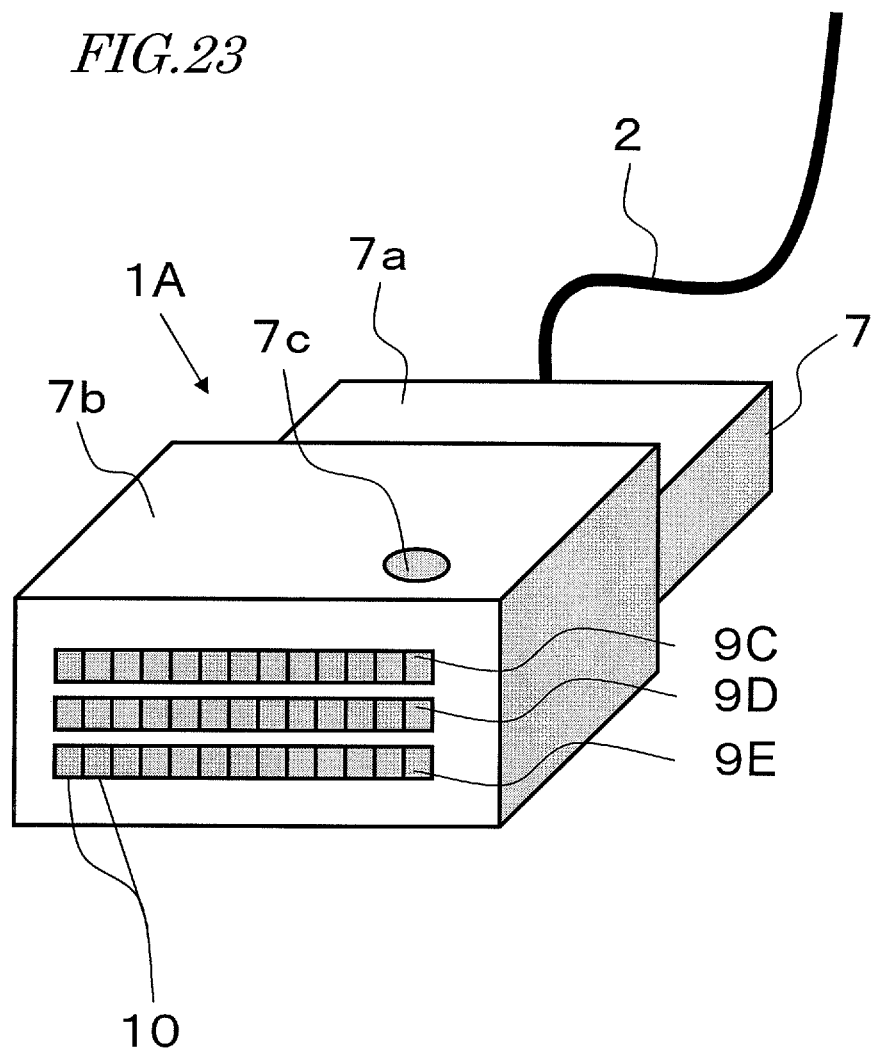
FIG. 23 is a perspective view generally illustrating a probe for use in the fourth preferred embodiment.

FIG. 23 illustrates the probe 1A for use in this preferred embodiment. As shown in FIG. 23, an array 9D of transducers, another array 9C of transducers, and a third array 9E of transducers are arranged parallel to each other inside the body case 7. By holding these three arrays of transducers, three tomographic images can be generated.

In the preferred embodiment to be described below, only the detection mode is supposed to be carried out without performing the positioning mode by a user who is not a skilled person but can still put the probe at a right position to render the subject's carotid artery.

The relative position of the probe with respect to the three tomographic images representing the blood vessel, which have been generated based on the echo signals received by the arrays 9C, 9D and 9E of transducers, is also as shown in FIG. 11 as already described for the first preferred embodiment. By using the probe 1A of this preferred embodiment, the tomographic images shown in FIGS. 12 to 15 can be obtained, for example. Thus, the IMT measuring range setting section 18 estimates the smoothness of the media-adventitia and lumen-intima boundaries 4J and 4K and the signal intensity around those boundaries and sets a range to detect the IMT value.

In FIG. 12, the media-adventitia and lumen-intima boundaries 4J and 4K are caught definitely in a right-hand-side portion of FIG. 12(b), a central portion of FIG. 12(c) and a left-hand-side portion of FIG. 12(d). That is why such an image will be an appropriate image for measuring the IMT. If the three images shown in FIGS. 12(b), 12(c) and 12(d) are used in combination, the region between the media-adventitia and lumen-intima boundaries 4J and 4K can be located with a predetermined length represented as a whole by overlapping the three images shown in FIGS. 12(b), 12(c) and 12(d) with each other. As a result, the IMT value can be detected.

Also, in FIG. 14, the region between the media-adventitia and lumen-intima boundaries 4J and 4K can be located easily in the entire image shown in FIG. 14(c) (i.e., from its left end through its right end), and therefore, the IMT value can be detected.

Furthermore, in FIG. 15, the media-adventitia and lumen-intima boundaries 4J and 4K are caught definitely in a left-hand-side portion of FIG. 15(b), a central portion of FIG. 15(c) and a right-hand-side portion of FIG. 15(d). Thus, combining these three image portions shown in FIGS. 15(b), 15(c) and 15(d) with each other, the region between the media-adventitia and lumen-intima boundaries 4J and 4K can be located as a whole and the IMT value can be detected.

On the other hand, in FIG. 13, neither the media-adventitia boundary 4J nor the lumen-intima boundary 4K is caught clearly in FIG. 13(b) but the media-adventitia and lumen-intima boundaries 4J and 4K are caught clearly only in a right-hand-side portion shown in FIG. 13(c) and in a central portion shown in FIG. 13(d). That is why even if those image portions shown in FIGS. 13(b), 13(c) and 13(d) are combined with each other, the region between the media-adventitia and lumen-intima boundaries 4J and 4K cannot be located and the IMT value cannot be detected as a result.

The IMT calculating section 20 calculates the IMT value based on such a principle of operation. And the information thus obtained is displayed on the monitor 4.

If the probe of this preferred embodiment is used, there is no need to move (or swing) the array of transducers, and therefore, the cost of the probe can be cut down. In addition, the thickness of the probe as measured in the short-axis direction can also be reduced.

Figure 24:
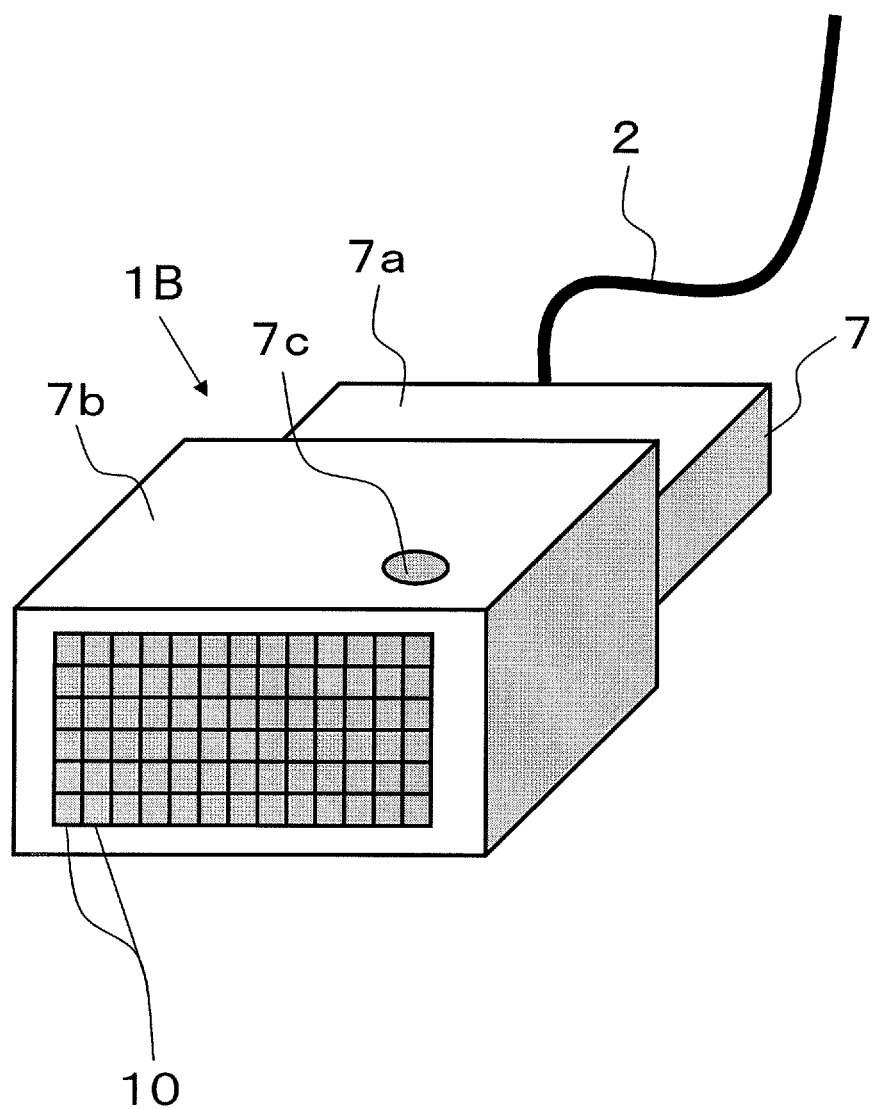
FIG. 24 is a perspective view generally illustrating an alternative probe, which may be used in the fourth preferred embodiment.

In the preferred embodiment described above, a probe in which three arrays of transducers are arranged parallel to each other as shown in FIG. 24 is supposed to be used. Alternatively, more than three tomographic images may be obtained and the IMT may be measured by using a probe 1B in which an even greater number of transducers are arranged two-dimensionally.

According to this preferred embodiment, the IMT may also be measured based on the echo data that has not been transformed into an image yet.

Embodiment 5

Figure 25:
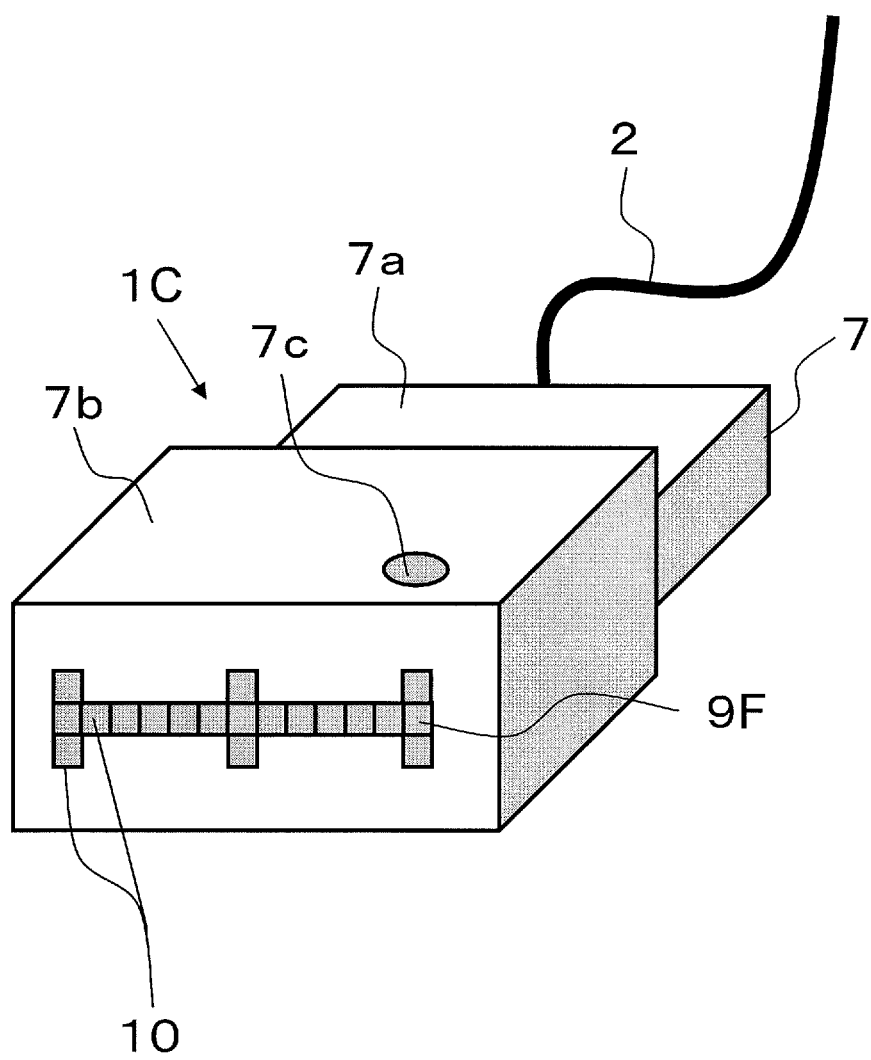
FIG. 25 is a perspective view generally illustrating a probe for use in the fifth preferred embodiment.

In the first and second preferred embodiments of the present invention described above, in the positioning mode in which the probe 1 needs to be put at a right position with respect to the carotid artery 6, the single array 9 of transducers is moved (or swung) to the right and left on its axis of rotation as shown in FIGS. 2 and 3, thereby obtaining echo data representing short-axis tomographic images of the blood vessel. However, such echo data representing the short-axis tomographic images can also be obtained by arranging some transducers perpendicularly to a single array 9F of transducers as shown in FIG. 25.

Figure 26:
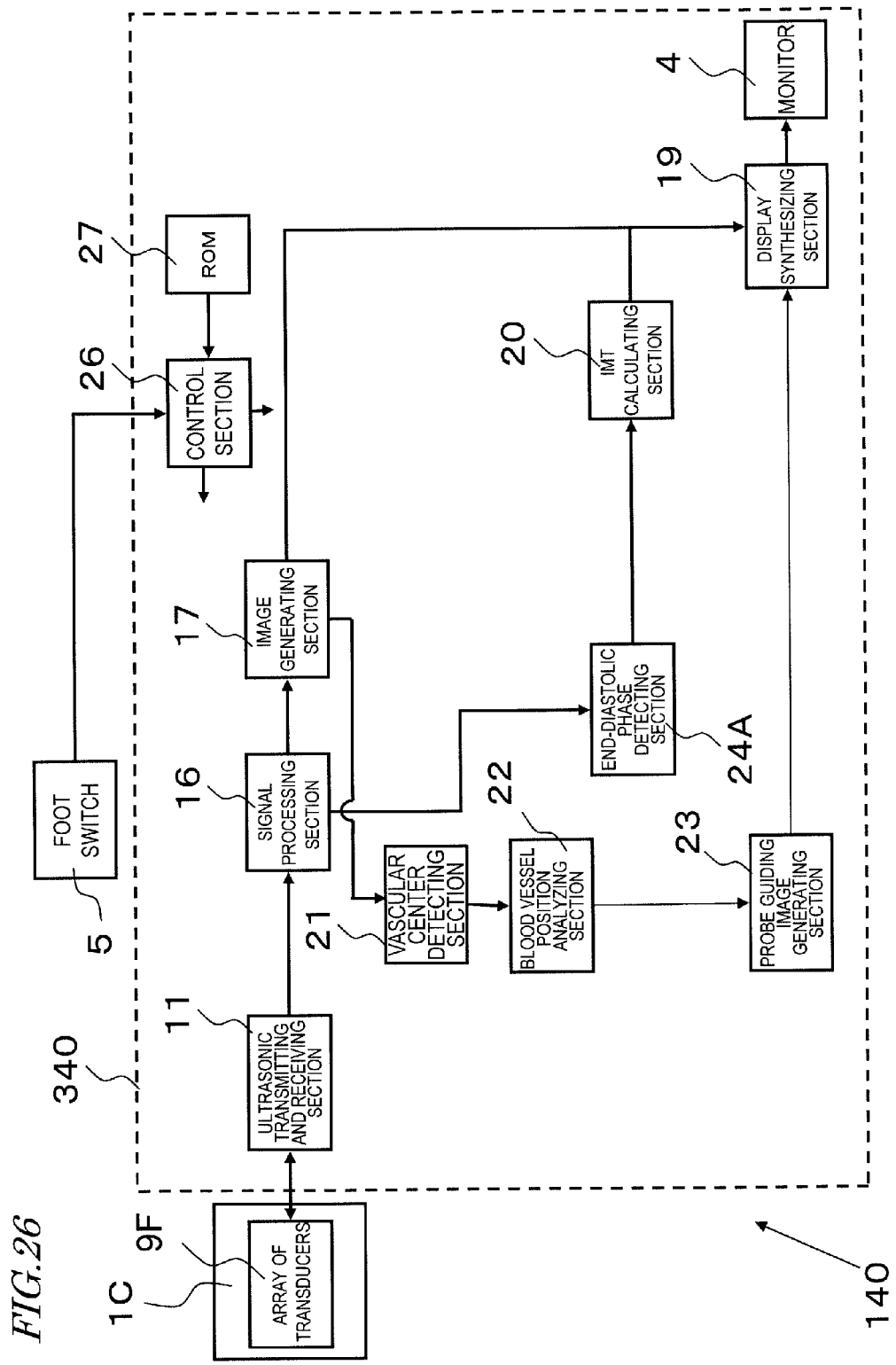
FIG. 26 is a block diagram illustrating the electrical configuration of an ultrasonic diagnostic apparatus 140 as a fifth preferred embodiment of the present invention.

FIG. 26 is a block diagram illustrating the electrical configuration of an ultrasonic diagnostic apparatus 140 as a fifth specific preferred embodiment of the present invention. The ultrasonic diagnostic apparatus 140 includes a probe 1C, a controller 340, the monitor 4, and the foot switch 5. As shown in FIG. 26, the ultrasonic transmitting and receiving section 11 is connected to the array 9F of transducers of the probe 1C.

In the ultrasonic diagnostic apparatus 140 shown in FIG. 26, any component also included in the ultrasonic diagnostic apparatus 100 or 110 of the first or second preferred embodiment and having substantially the same function as its counterpart is identified by the same reference numeral and its description will be omitted herein.

According to this preferred embodiment, the transducers that are arranged perpendicularly to the array 9F of transducers of the probe 1C receive signals from the short-axis cross sections L1, L2 and L3 shown in FIG. 6. Then, the received signals are transformed into images by the ultrasonic transmitting and receiving section 11, the signal processing section 16 and the image generating section 17, which are processed by the display synthesizing section 19 and then presented as short-axis tomographic images in the short-axis image display area 4B shown in FIG. 8. On the other hand, the long-axis image to be displayed in the long-axis image display area 4A shown in FIG. 8 has been generated by the ultrasonic transmitting and receiving section 11, the signal processing section 16 and the image generating section 17 based on the signal received by the array 9F of transducers and displayed after having been processed by the display synthesizing section 19.

Next, by taking advantage of the fact that the carotid artery 6 has an almost circular cross section, the vascular center detecting section 21 locates the center axis of the blood vessel based on the short-axis tomographic images generated by the image generating section 17 and then compares the center axis of the blood vessel to the blood vessel centering guide line 4C shown in FIG. 8, thereby calculating the magnitude of shift between them. In the status shown in FIG. 8, cross sections of two branches of the carotid artery 6 appear in the short-axis tomographic image S1 and the center axis of the carotid artery 6 is aligned with the blood vessel centering guide line 4C that defines the centerline of the short-axis tomographic images S2 and S3. Consequently, it can be said that the probe 1 is now arranged at a right position for detection.

However, if the center axis of the blood vessel that has been detected by the vascular center detecting section 21 has shifted with respect to the blood vessel centering guide line 4C, then the blood vessel position analyzing section 22 checks the relative position of the probe 1C with respect to the carotid artery 6 by examining where the two branches of the carotid artery are located on the short-axis tomographic image S1 and to which side of the blood vessel centering guide line 4C the center axis of the blood vessel has shifted on the short-axis tomographic images S2 and S3. Then, the probe guiding image generating section 23 generates the improperly tilted positioning image 4D shown in FIGS. 9 and 10. The improperly tilted positioning image 4D not only indicates how much the probe 1C is improperly tilted with respect to the carotid artery 6 but also prompts the user to adjust the position of the probe 1C so that the probe 1C is arranged exactly parallel to the carotid artery 6. Thus, the user scans the object with the probe 1C while monitoring the improperly tilted positioning image 4D.

If the probe 1 has been put at a right position on the subject so that the center axis of the carotid artery 6 is aligned with the blood vessel centering guide line 4C, then the control section 26 may sense that the positioning has been done successfully. Alternatively, in response to a user's notification that has been entered with an input device, the end-diastolic phase detecting section 24A may detect the end of the diastolic phase. After that, the IMT calculating section 20 carries out IMT measurement using the long-axis tomographic image that has been generated based on the signal received from the array 9F of transducers.

If the probe of this preferred embodiment is used, there is no need to move (or swing) the array of transducers and the number of transducers to use can be reduced. As a result, the cost of the probe can be cut down. In addition, the thickness of the probe as measured in the short-axis direction can also be reduced.

Optionally, the probe of the preferred embodiment described above may be replaced with a so-called "matrix probe" in which a number of transducers are arranged in at least three lines in the same direction so as to form a matrix pattern as a whole.

INDUSTRIAL APPLICABILITY

According to the present invention, even if the probe has not been put in an exactly right position to face the region of interest squarely, a detected value can also be obtained from that region of interest. As a result, even an unskilled person can get the detection done reasonably accurately. For that reason, the ultrasonic diagnostic apparatus obtained by carrying out the present invention accepts users with various levels of skills or experience and can be used effectively as an apparatus with good operability.

The present invention can be used extensively to inspect the status of a subject's carotid artery, for example.

REFERENCE SIGNS LIST 1 probe
1A, 1B, 1C probe
2 cable
3 controller
4 monitor
5 foot switch
6 carotid artery
7 body case
7a grip portion
7b contact portion
7c probe origin marker
8 axis of swing
9, 9A, 9B, 9C, 9D, 9E, 9F array of transducers
10 ultrasonic transducer
11 ultrasonic transmitting and receiving section
12 transmission-reception control section
13 swinging section
14 swing control section
15 operation-mode management section
16 signal processing section
17 image generating section
18 IMT measuring range setting section
19 display synthesizing section
20 IMT calculating section
21 vascular center detecting section
22 blood vessel position analyzing section
23 probe guiding image generating section
24 end-diastolic phase detecting section 25 electrocardiogram checking section
26 control section
27 ROM
100, 110, 130, 140 ultrasonic diagnostic apparatus

The invention claimed is:

1. An ultrasonic diagnostic apparatus comprising a controller, a monitor, and a probe, wherein a first direction and a second direction are defined relative to the probe, the second direction intersecting the first direction at right angles, the probe having a plurality of arrays of transducers, in which the transducers are arranged in the first direction, or having a swinging section with an array with a number of transducers arranged in the first direction, the array swinging in the second direction that intersects with the first direction at right angles,
wherein the controller transmits an ultrasonic beam from the array or the plurality of arrays of the probe to a subject, generates a number of tomographic images using image data based on an echo signal received from the subject, detects a section of a blood vessel wall in which a thickness measurement is possible in each of the tomographic images, and if a sum of lengths of the detected sections of the blood vessel wall in the each of the tomographic images is equal to or greater than a predetermined value, calculates the thickness of the blood vessel wall by combining the number of tomographic images,
wherein the controller has a detection mode in which the blood vessel wall is detected, and in the detection mode, the controller calculates the thickness of the blood vessel wall, and
wherein the monitor displays an image based on the image data that has been generated by the controller.

2. The ultrasonic diagnostic apparatus of claim 1, wherein the controller has a positioning mode to be carried out before the detection mode, and
wherein in the positioning mode, the controller gets echo signals received from multiple points of the blood vessel and generates not only image data representing the blood vessel based on the echo signal but also image data representing the tilted positioning which indicates how much the probe is tilted with respect to the blood vessel, and
wherein based on the image data detected, the monitor displays the image representing the blood vessel and the image representing the tilted positioning.

3. The ultrasonic diagnostic apparatus of claim 2, wherein the image representing the tilted positioning includes a centerline representing the center axis of the blood vessel to be detected by the probe and a probe symbol indicating how much the probe is tilted with respect to the centerline.

4. The ultrasonic diagnostic apparatus of claim 3, wherein a probe origin marker has been set on the probe, and
wherein the probe symbol includes a probe origin that corresponds to the probe origin marker and that indicates a position on the image representing the tilted positioning.

5. The ultrasonic diagnostic apparatus of claim 4, wherein the probe origin marker of the probe is set at an end of the array of transducers.

6. The ultrasonic diagnostic apparatus of claim 3, wherein on the image representing the tilted positioning, detectable lines, representing a range where the blood vessel is detectable, are rendered on both sides of the centerline of the blood vessel.

7. The ultrasonic diagnostic apparatus of claim 2 wherein in the positioning mode, the controller generates not only image data for positioning based on an echo signal that has been obtained by sending an ultrasonic beam in the second direction with some of the transducers in the array or the plurality of arrays controlled but also first image data for detection of the blood vessel based on an echo signal that has been obtained by sending an ultrasonic beam in the first direction with the other transducers in the array or the plurality of arrays controlled,
wherein in the detection mode, the controller generates second image data for detection of the blood vessel by controlling all transducers in the array or the plurality of arrays, and
wherein the monitor displays the image for detection based on the second image data for detection.

8. The ultrasonic diagnostic apparatus of claim 7, wherein those transducers, that are used in the array or the plurality of arrays to generate the image for positioning, scan the body with an ultrasonic beam either mechanically or by deforming a material, the material being deformed with an applied voltage, and the material being arranged on a first surface of the array or the plurality of arrays so as to face the body or arranged on a second surface of the array or the plurality of arrays that is opposite from the first surface of the array or the plurality of arrays.

9. The ultrasonic diagnostic apparatus of claim 8, wherein the material deformed with the applied voltage is a conductive high molecular material, an ionic conductive high molecular material or a dielectric elastomer.

10. The ultrasonic diagnostic apparatus of claim 7, wherein the monitor further renders a guideline for positioning on the image for positioning.

11. The ultrasonic diagnostic apparatus of claim 7, wherein the array or the plurality of arrays of the probe includes multiple subsets of transducers, each said subset being used to generate the image for positioning, and
wherein the controller generates image data for positioning that is associated with either each said subset of transducers or only selected subsets of transducers, and
wherein the monitor displays the image for positioning based on each said image data for positioning.

12. The ultrasonic diagnostic apparatus of claim 1, wherein the probe has the plurality of arrays of transducers, which are arranged in three parallel lines in the first direction, and generates the number of tomographic images by the number of arrays of transducers.

13. The ultrasonic diagnostic apparatus of claim 1, wherein the probe includes the swinging section that swings the array of transducers under the control of the controller, and generates the number of tomographic images by a number of swing angles.

14. The ultrasonic diagnostic apparatus of claim 13, wherein the swinging section swings the array of transducers on the axis of swing in accordance with an instruction given by the controller so that the array defines a predetermined swing angle with respect to the center of swing of the array of transducers, and
wherein the controller controls swinging so that the swing angle of the array of transducers becomes greater in the positioning mode than in the detection mode.

15. A method of displaying an image representing a region of interest using an ultrasonic diagnostic apparatus, the method comprising the steps of:
putting the probe of the ultrasonic diagnostic apparatus of claim 14 on a body of the subject;

displaying, on the monitor, an image representing how much the probe is tilted with respect to the region of interest of the body based on image data representing the tilted positioning;

adjusting the position of the array of transducers based on an image representing the tilted positioning to be displayed on the monitor either while the array of transducers is being moved or after the array of transducers has been moved; and displaying the image of the region of interest on the monitor based on the image data of the region of interest.

16. The method of claim 15, wherein the step of putting includes putting the probe on a neck of the body, and wherein the step of displaying the image of the region of interest includes displaying an image representing a carotid artery.

17. The ultrasonic diagnostic apparatus of claim 1, wherein the probe includes ultrasonic transducers, which are arranged in three or more lines at least in the first direction so as to form a matrix pattern as a whole.

18. A method of controlling an ultrasonic diagnostic apparatus, to which a monitor is connectable, and a probe, wherein a first direction and a second direction are defined relative to the probe, the second direction intersecting the first direction at right angles, the probe having a plurality of arrays of transducers, in which the transducers are arranged in the first direction, or having a swinging section with an array with a number of transducers arranged in the first direction, the array swinging in the second direction that intersects with the first direction at right angles, the method comprising the steps of:

transmitting an ultrasonic beam from the array or the plurality of arrays of the probe to a subject;

generating a number of tomographic image using image data based on an echo signal received from the subject;

detecting a section of a blood vessel wall in which a thickness measurement is possible in each of the tomographic images;

if a sum of length of the detected sections of the blood vessel wall in the each of the tomographic images is equal to or greater than a predetermined value, then calculating the thickness of the blood vessel wall by combining the number of tomographic images;

displaying an image indicating relations of a slant position in the monitor based on slant position relations image data indicating how much the transducers are tilted relative to the blood vessel;

adjusting the movement of the transducers based on the image indicating the relations of the slant position displayed by the monitor with the plurality of arrays or swinging of the transducers; and displaying an image of the blood vessel in the monitor based on an image data of the blood vessel.

* * * * *